(12) United States Patent
Littrup et al.

(10) Patent No.: US 9,095,320 B2
(45) Date of Patent: Aug. 4, 2015

(54) CRYO-INDUCED RENAL NEUROMODULATION DEVICES AND METHODS

(75) Inventors: Peter Littrup, Bloomfield Hills, MI (US); Alexei Babkin, Albuquerque, NM (US); Barron Nydam, Rancho Santa Fe, CA (US); William Nydam, Rancho Santa Fe, CA (US)

(73) Assignee: CyroMedix, LLC, San Diego, CA (US)

( * ) Notice: Subject to any disclaimer, the term of this patent is extended or adjusted under 35 U.S.C. 154(b) by 944 days.

(21) Appl. No.: 13/246,120

(22) Filed: Sep. 27, 2011

(65) Prior Publication Data

US 2012/0253336 A1    Oct. 4, 2012

Related U.S. Application Data

(63) Continuation-in-part of application No. PCT/US2011/049287, filed on Aug. 26, 2011.

(60) Provisional application No. 61/386,870, filed on Sep. 27, 2010.

(51) Int. Cl.
*A61B 18/20* (2006.01)
*A61B 18/02* (2006.01)
*A61B 18/00* (2006.01)

(52) U.S. Cl.
CPC ......... *A61B 18/02* (2013.01); *A61B 2018/0022* (2013.01); *A61B 2018/00404* (2013.01); *A61B 2018/00434* (2013.01); *A61B 2018/00511* (2013.01); *A61B 2018/00589* (2013.01); *A61B 2018/0212* (2013.01); *A61B 2018/0268* (2013.01)

(58) Field of Classification Search
CPC .................... A61B 18/02; A61B 2018/0212
USPC ............................................. 606/21
See application file for complete search history.

(56) References Cited

U.S. PATENT DOCUMENTS 5,305,825 A    4/1994  Roehrich et al.
5,741,248 A *  4/1998  Stern et al. .................. 606/21
(Continued)

FOREIGN PATENT DOCUMENTS

AU    2004201679    5/2004
WO    92/04872      4/1992
(Continued)

*Primary Examiner* — Alyssa M Alter
(74) *Attorney, Agent, or Firm* — Convergent Law Group LLP; Rick Batt

(57) ABSTRACT

A method for cryo-induced renal neuromodulation includes applying cryoenergy to neural fibers that contribute to renal function, or to vascular structures that contact, feed or perfuse the neural fibers. In one embodiment, cryoenergy is applied via a distal energy-delivering section of a flexible catheter. The distal section may include a plurality of microtubes for transporting a cryogen to the distal tip. The energy-delivering section contacts and extracts heat from the wall of the renal artery. In one embodiment, the distal energy-delivering section is radially expandable. The renal nerve is cooled to a degree such that nerve function is disrupted.

41 Claims, 14 Drawing Sheets

(56) References Cited

U.S. PATENT DOCUMENTS

| | | |
|---|---|---|
| 6,679,081 B2 | 1/2004 | Marsala |
| 7,617,005 B2 | 11/2009 | Demarais et al. |
| 2005/0261753 A1* | 11/2005 | Littrup et al. .................. 607/96 |
| 2007/0112251 A1 | 5/2007 | Nakhuda |
| 2007/0112327 A1* | 5/2007 | Yun et al. ...................... 604/500 |
| 2008/0119834 A1 | 5/2008 | Vancelette et al. |
| 2008/0119839 A1 | 5/2008 | Vancelette et al. |
| 2008/0125764 A1 | 5/2008 | Vancelette et al. |
| 2009/0270851 A1 | 10/2009 | Babkin |

FOREIGN PATENT DOCUMENTS

| | | |
|---|---|---|
| WO | 00/09054 | 2/2000 |
| WO | 2004/064914 | 8/2004 |
| WO | 2005/063136 | 7/2005 |
| WO | 2009/067497 | 5/2009 |
| WO | 2009/131978 | 10/2009 |

\* cited by examiner

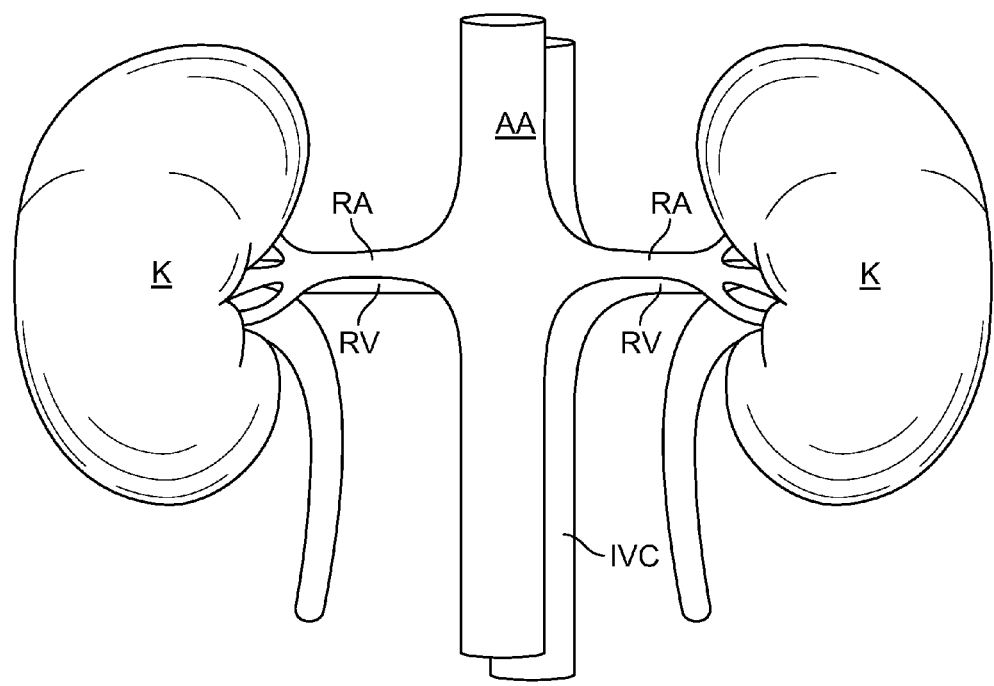
FIG. 1A
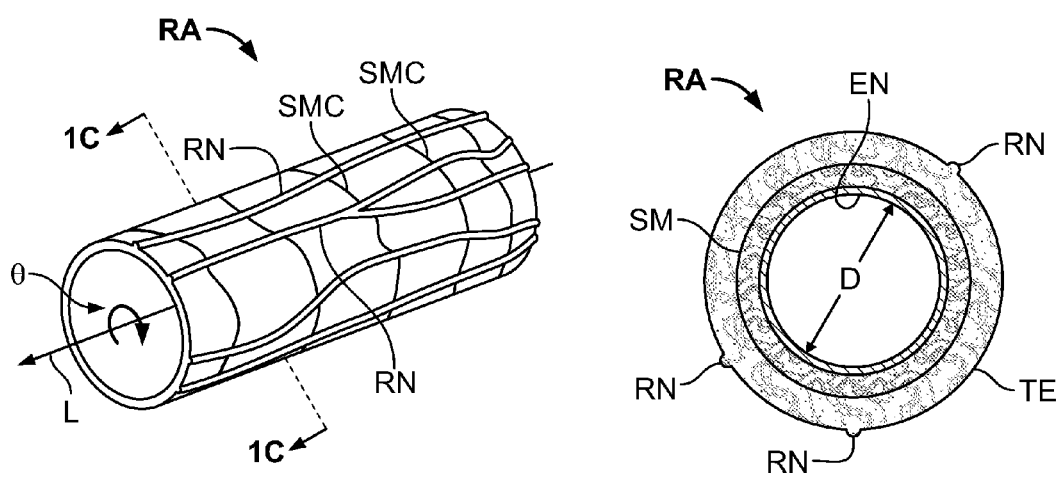
FIG. 1B
FIG. 1C

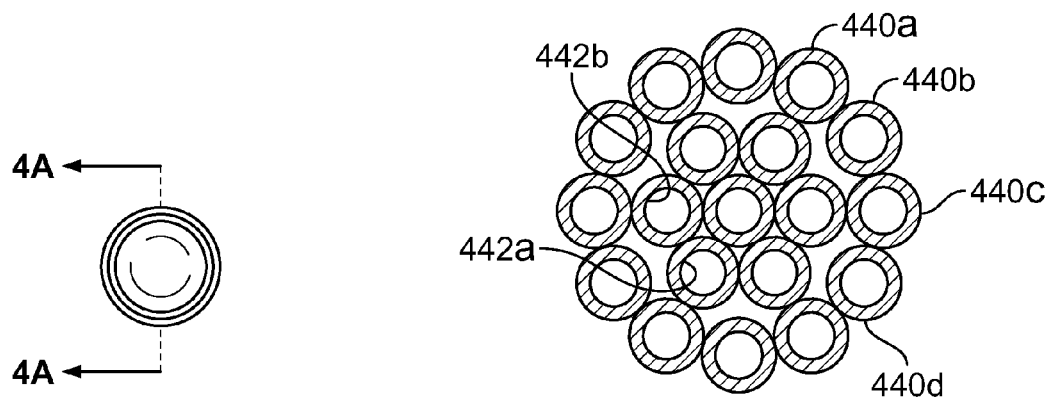
FIG. 4D
FIG. 4E
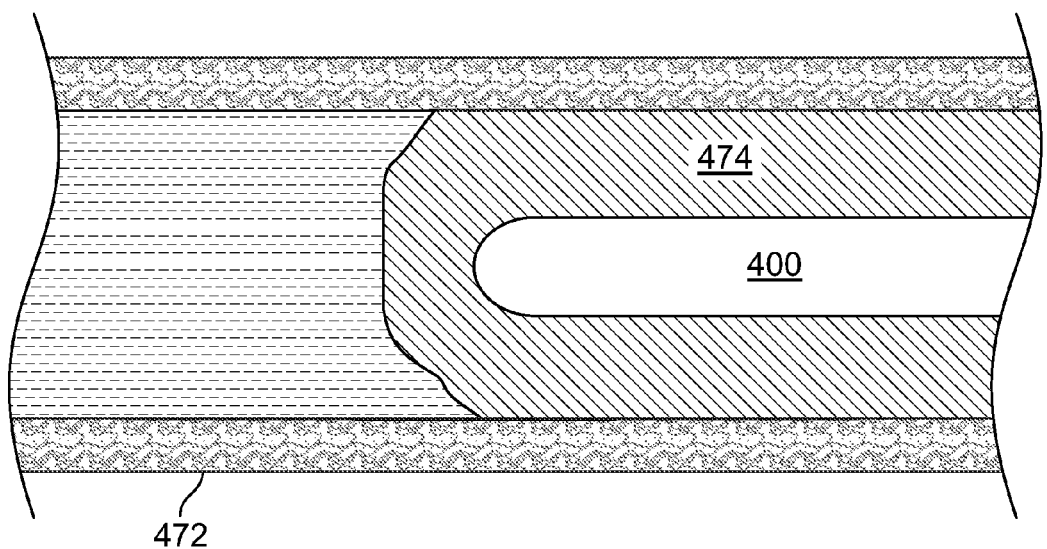
FIG. 4F

CRYO-INDUCED RENAL NEUROMODULATION DEVICES AND METHODS

CROSS-REFERENCE TO RELATED APPLICATIONS

The present application claims the benefit of provisional patent application No. 61/386,870 filed Sep. 27, 2010, entitled "Renal Neuromodulation via Cryoablation of the Renal Nerve". The present application is a continuation in part of international patent application no. PCT/US11/49287, filed Aug. 26, 2011, entitled "Cryoablation Balloon Catheter and Method".

BACKGROUND OF THE INVENTION

This invention relates to a device and methods for renal nerve modulation, and more particularly, to ablation of the renal nerve using thermal energy.

Radiofrequency (RF) based thermal energy has been shown to effectively ablate nerves, and therefore prevent neurological impulses from crossing the ablated region. For patients with high blood pressure (BP), or hypertension (HTN), RF neuromodulation has been demonstrated to lower their BP (See, e.g., References 1-9 herein). Reducing a patient's BP may be particularly important if they have resistant HTN, whereby even multiple medications are insufficient to produce controlled systolic and diastolic pressures below 140 and 90 mm Hg, respectively.

RF neuromodulation, however, has potential negative side effects. Because RF devices achieve ablation via delivering heat, the device destroys nerve function by burning or cooking the axons running with the renal artery. Though this produces the desired effect on the nerve, the heat produced by the RF device causes pain and must be delivered from the tip of the catheter, requiring multiple ablations in different segments of the artery to avoid circumferential impact upon the renal artery wall and/or its lining RF ablation has been shown to cause scarring, strictures and clotting, or thrombosis, in other vessels.

Most notably, RF ablations surrounding the pulmonary vein within the right atrium of the heart to eliminate cardiac arrhythmias has caused strictures of the pulmonary vein with severe consequences. Therefore, to avoid renal artery strictures, or stenoses, circumferential RF ablation inside the renal artery to cause neural modulation is currently avoided by performing RF ablation in quadrants, along different segments of the renal artery. However, it is unknown whether the untreated quadrants may give rise to future greater relapse rates of HTN due to regrowth of the renal nerve in the non-ablated quadrants.

In addition, adjacent tissues in the kidneys, the collecting system for urine, have been subject to problematic scarring and strictures when RF ablation has been used to treat cancerous kidney tumors.

There is thus a need for a less painful method to treat a circumferential, or near-circumferential, segment of one or more renal arteries without the known risks associated with the RF ablation as described above.

Various patents describe renal neuromodulation by use of cold temperatures below 0° C. to produce some nerve dysfunction, at least for a transient period. See U.S. Pat. Nos. 7,617,005; 7,717,948; and 7,853,333. However, these patents describe only one embodiment that used Peltier thermoelectric cooling to produce nerve dysfunction. While thermoelectric cooling may be feasible within a catheter, it is unlikely to produce the sufficient low temperatures needed for durable renal nerve ablation.

Cryoablation, or freezing of tissue to lethal temperatures, has been used for tissue ablation in many locations within the body, mainly for tumors. Current cryotechnology using the Joule-Thompson effect, or JT cooling, produced by rapidly expanding gases, can achieve target temperatures within tissue of −40° C. However, the actual cooling capacity, or power, is quite limited due to the inefficiencies of cooling with a cryogen in a predominant gaseous state (e.g., thermal conductivity of gases is much less than liquids). This severely limits the propagation of sufficient lethal temperatures into tissues surrounding a cryoprobe, even when the surface of a JT cryoprobe using argon can be as low as −150° C. at the surface.

The above mentioned shortcoming in current JT cryoprobes becomes particularly evident in high heat sink scenarios, such as moving liquid or blood in a vessel, whereby a current JT cryoprobe doesn't have the capacity to form ice around the probe. Thereby, the current JT cryotechnology is generally ineffective to sufficiently propagate ice into tissue surrounding a blood vessel.

In addition, the high pressures required for argon-based JT cooling (e.g., 2000 PSI pressure drop) precluded its use within catheters, whereby their nonmetallic walls are generally rated only up to 500 PSI.

Since cooling of Argon gas occurs at the JT nozzle within an expansion chamber, producing a circumferential ablation of reasonable length (e.g., >1 cm) would be very difficult. The expansion chamber at the tip of the catheter would need to be similar to those used inside current metal cryoneedles or probes and would cause limited cooling.

A previous solution to the high pressure required in argon-based JT cooling is the use of nitrous-oxide cryogens. JT cooling can be done within a catheter using a cryogen which requires a much lower pressure drop, such as nitrous oxide. However, nitrous oxide generally only produces cooling at the tip of the cryoprobe/catheter surface of no lower than −60° C. In addition, cryoplasty research acknowledges that it is not possible to get much colder than −10° C. at the balloon surface, let alone into the surrounding artery wall.

Another cryoablation system uses a fluid at a near critical or supercritical state. Such cryoablation systems are described in U.S. Pat. Nos. 7,083,612 and 7,273,479. These systems have some advantages over previous systems. The benefits arise from the fluid having a gas-like viscosity. Having operating conditions near the critical point of nitrogen enables the system to avoid the undesirable phenomena of vapor lock associated with JT cooling while still providing good heat capacity. Additionally, such cryosystems can use very small channel probes and operate at pressures below 500 PSI for use in non-metal catheters.

However, challenges arise from use of a near-critical cryogen in a cryoablation system. In particular, there is still a significant density change in nitrogen (about 8 times) once it is crossing its critical point—resulting in the need for long pre-cooling times of the instrument. The heat capacity is high only close to the critical point and the system is very inefficient at higher temperatures requiring long pre-cooling times. Additionally, the system does not warm up (or thaw) the cryoprobe efficiently. Additionally, near-critical cryogen systems require a custom cryogenic pump(s) which is more difficult to create and service.

Still other types of thermo-based ablation systems are described in the patent literature. U.S. Pat. Nos. 5,957,963; 6,161,543; 6,241,722; 6,767,346; 6,936,045; 7,617,005 and International Patent Application No. PCT/US2008/084004, filed Nov. 19, 2008, describe various thermo-based ablation probes including malleable and flexible cryoprobes. Examples of patents describing cryoablation systems for supplying liquid nitrogen, nitrous oxide, argon, krypton, and other cryogens or different combinations thereof combined with Joule-Thomson effect include U.S. Pat. Nos. 5,520,682; 5,787,715; 5,956,958; 6074572; 6,530,234; and 6,981,382.

Notwithstanding the above, a cryotechnology system is desirable that has: 1.) sufficient cooling to cause renal neuromodulation, 2.) an operating size and shape to be used with an endovascular catheter of preferably less than 3 mm diameter (i.e., 9 French) and 3.) the ability to cause circumferential and/or partial circumferential intense cooling of the artery wall.

Various cryo-energy delivering balloon catheters have been described in the patent literature. U.S. Pat. No. 6,736, 809, for example, is directed to a method for treating an aneurysm by cooling a target tissue region of the aneurysm to a temperature below a target temperature for a preselected time period. The method entails thickening, strengthening, or increasing the density of a blood vessel wall by cooling the blood vessel wall with a cryogenically cooled device. In particular, a device having a heat conductive cooling chamber is disposed proximate to the aneurysm site; and a cryogenic fluid coolant is directed to flow inside the chamber to create endothermic cooling relative to the aneurysm.

U.S. Pat. No. 6,283,959 is also directed to a cryo-energy delivery device. The device described in the '959 patent uses carbon dioxide ($CO_2$) and has a metallic balloon surface with different patterns for greater thermal conductivity. The '959 patent describes use of a non-toxic fluid to fill the balloon such as $CO_2$, or nitrous oxide ($N_2O$), in case of balloon rupture. The '959 patent also describes use of evaporative and JT cooling aspects by injecting a predominant liquid mixture under pressure and allowing evaporation and gas expansion. In addition, these gases are generally functional within the engineering constraints of most balloons and catheters of less than 500 psi pressure. However, with $CO_2$ and $N_2O$ having respective boiling points of −78.5° C. and −88.5° C., the surface temperatures of a balloon in contact with a vessel wall inside the high heat load region of a blood vessel generally achieves only −10° C. as previously noted from cryoplasty experience. It is therefore uncertain, or perhaps unlikely, that any of the desired "positive remodeling" needed to keep an artery open to its balloon-dilated extent would be possible since temperatures required to get this stent-like effect need to be less than −40° C. See references 10,11 herein.

This has implications for the renal artery which can have stenoses that actually cause "renal" hypertension by means of what was originally thought to be solely a compensatory response of the renin-angiotensin hormone system releasing these hormones in response to apparent low blood pressure within the renal artery and/or a kidney distal to the stenosis, thus causing overall hypertension in the remainder of the body to just keep the pressure gradient within the kidney. This is as opposed to "essential" hypertension in patients with more normal appearing renal artery lumens. Of note, large trials assessing blood pressure responses to extensive use of angioplasty and stents for renal artery stenoses in patients with resistant hypertension within the last two decades found no significant improvement in overall hypertension levels. Therefore, while the renin-angiotensin system may play an initial compensatory role, there is still the need for a technology and method which treats long-term persistent hypertension after angioplasty and/or stenting.

Renal artery stenting in many patients with hypertension also raises the issue of RF ablation being incompatible with the metal stents in most of these patients. A new technology is needed which can effectively cause renal sympathetic nervous system (RSNA) modulation while also contributing to some aspect of positive remodeling of the renal artery lumen in patients with stenosis, or especially in patients with indwelling prior metal stents.In addition, if nerve ablation is desired for treating hypertension by ablating the renal nerve within and/or surrounding the renal artery wall, temperatures of −60° C. or below may be needed for long-term prevention of renal nerve regrowth that may impact the long-term duration of lowered blood pressure after ablation. Therefore, it is uncertain, if not unlikely, that the above described cryo-balloons can achieve the desired temperatures within a biological system because of the physical limitations necessary for evaporative or JT-based cryosystems.

The above mentioned '809 and '959 patents do not describe a design for the generation of sufficiently low temperatures to obtain the desired cryo-physiologic response. Insufficient generation of cold temperatures arise from the physical limitations of the cooling mechanisms, as well as the physical engineering limitations, proposed in the above mentioned patents.

An improved cryoablation catheter and/or associated balloon configuration that achieves minimal temperatures of less than −40° C. within several millimeters of the balloon and/or endoluminal surface of the vessel wall, is desirable to achieve desired vascular effects from positive remodeling. This is desirable in treating, for example, aneurysms, and to treat hypertension by renal nerve ablation.

A cryoablation balloon catheter design is desirable that achieves the necessary therapeutic temperatures within the engineering and anatomical constraints.

A method that has a substantially greater cooling power than is currently attainable through JT cooling to overcome the heat sink of the flowing blood within the renal artery, and to penetrate a thickened, atherosclerotic renal artery wall is therefore desirable.

SUMMARY OF THE INVENTION

A method for renal neuromodulation extracts heat from the tissue within and/or surrounding the renal artery, particularly the nerve cells running along, or within, the wall of the renal artery. The tissue is frozen to a sufficient target temperature such that the conducting segments, or axons, of these nerves are destroyed or defunctionalized thereby removing and/or modulating sympathetic nerve control of the kidney.

In another embodiment, a method for treating the renal nerve with cryoenergy comprises the steps of: navigating a distal cryoenergy delivery section of a cryoablation catheter through the vasculature and into the renal artery to a first location in proximity of the renal nerve; contacting the wall of the renal artery with the distal cryoenergy delivery section; and cooling the wall of the renal artery to a first temperature such that nerve function is disrupted. The step of cooling is carried out by transporting a cryogen in a liquid-only state to and from the distal cryoenergy delivery section.

In another embodiment, the distal cryo energy delivery section is an uninsulated portion of the catheter and/or microtubules. Single phase liquid cooling causes the lumen to be more rapidly occluded by ice due to its high freeze capacity or power than any JT-based cooling. The ice efficiently transmits the intense cryo temperatures circumferentially to the surrounding arterial wall. Blood flow within the artery without apparent thrombosis is reestablished as observed by angiography after a short time period (e.g., approximately 2 min.) of thawing.

In another embodiment the rate of thawing after the freeze is controlled by warming of the cryogen to expedite reestablishment of normal renal blood flow. The step of thawing may comprise warming the cryogen to up to 43 degrees C.

In another embodiment, the contacting step may be carried out by expanding an expandable structure associated with the distal cryoenergy delivery section. Expanding may be carried out by expanding a balloon, or manipulation of a pull wire, that expands a multifilament segment for better contact with the artery wall. In one embodiment, the structure is radially expanded.

In another embodiment, the cooling step may be performed by cooling an entire circumferential portion of the renal artery wall, or in another embodiment by cooling a portion of the renal artery wall corresponding to an arcuate segment less than 360 degrees (e.g., 90-270°). The cryogen may be transported via a plurality of microtubes disposed on the inside, or outside, of the balloon.

In another embodiment, cryoenergy is applied to the renal artery such that a cytotoxic temperature is reached of at least less than −40° C., and in another embodiment of at least less than −60° C.

In another embodiment the cryoenergy is applied multiple times. At least two freezes are carried out at a temperature of less than −40 C. In another embodiment, three freezes are carried out.

In another embodiment the cryoenergy is applied within the renal artery such that the temperatures extend several millimeters beyond the luminal surface of, or balloon interface with, the renal artery in order to create full thickness penetration through the renal artery wall, even if it has been thickened by atherosclerosis and despite the heat sink effect of the flowing blood.

In another embodiment, ablation is carried out in multiple main renal arteries or their segmental branches.

In another embodiment, cryoablation is carried out to effectively cause positive remodeling of the artery lumen in patients with stenosis, or in patients with indwelling prior metal stents. Vessels to be remodeled include coronary, major, renal, and peripheral arteries. In one embodiment, cryoablation is carried out to cause renal sympathetic nervous system (RSNA) modulation while also contributing to some aspect of positive remodeling of the renal artery lumen in patients with stenosis, or especially in patients with indwelling prior metal stents.

The description, objects and advantages of the present invention will become apparent from the detailed description to follow, together with the accompanying drawings.

BRIEF DESCRIPTION OF THE DRAWINGS

FIG. 1A is a schematic representation of the renal anatomy.

FIG. 1B is an isometric view showing the renal nerves relative to the renal artery.

FIG. 1C is a cross sectional view showing the renal nerves relative to the vessel wall.

FIG. 4b is an enlarged view of the distal tip shown in FIG. 4a.

FIG. 4c is an enlarged view of the transitional section of the cryoprobe shown in FIG. 4a.

FIG. 4d is an end view of the cryoprobe shown in FIG. 4a.

FIG. 4e is a cross sectional view taken along line 4e-4e illustrating a plurality of microtubes for transporting the liquid refrigerant to and from the distal tip of the cryoprobe.

FIG. 4F is an illustration of a cryoablation multitubule catheter positioned inside a lumen.

DETAILED DESCRIPTION OF THE INVENTION

Figure 1D:
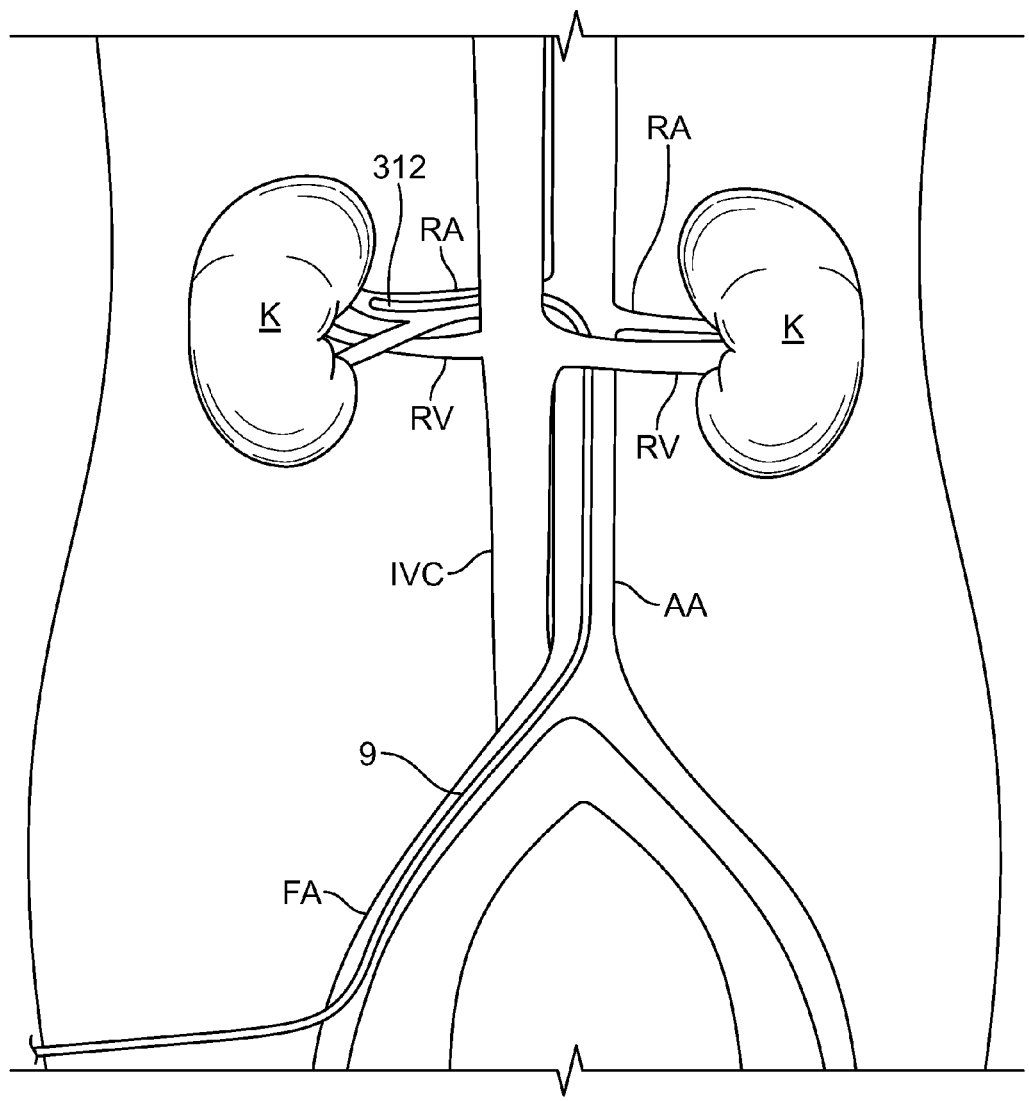
FIG. 1D is an illustration showing a cryoablation catheter extending through the vasculature and into the renal artery in a human body.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is also to be appreciated that unless defined otherwise, all technical and scientific terms used herein have the same meaning as commonly understood by one of ordinary skill in the art to which this invention belongs.

Described herein are methods for renal neuromodulation via thermal mechanisms to achieve a reduction in renal sympathetic nerve activity and in particular, a method for ablating the renal nerves lying within the wall and/or surrounding the renal artery using cryoenergy. Denervation of the kidneys serves to alter the complex role of the kidney in regulating blood pressure changes, thereby lowering blood pressure (BP).

To better understand the present invention, a schematic representation of the relevant renal anatomy is shown in FIGS. 1A to 1C.

Anatomy

With reference to FIG. 1A, the human renal anatomy includes the kidneys K, which are supplied with oxygenated blood by the renal arteries RA. The renal arteries are connected to the heart via the abdominal aorta AA. Deoxygenated blood flows from the kidneys to the heart via the renal veins RV and the inferior vena cava IVC.

FIG. 1B illustrates a portion of the renal anatomy in greater detail. More specifically, the renal anatomy also includes renal nerves RN extending longitudinally along the lengthwise dimension L of renal artery RA, generally within the adventitia and/or outer muscular layer of the artery wall. The renal artery RA has smooth muscle cells SMC that surround the arterial circumference and spiral around the angular axis θ of the artery.

FIG. 1C illustrates a cross sectional view of a renal artery RA. It is made up of several layers including an inner endothelial lining EN, a smooth muscle cells layer SM, and a tunica external TE (adventitia). The renal nerves are generally within or associated within this outer tunic layer, or the underlying muscular layers.

Renal Neuromodulation Method

A cryo-based renal neuromodulation procedure is illustrated in FIG. 1D.

First, access to the femoral artery FA is achieved by first puncture and then guide wire placement, commonly known as the Seldinger technique.

A guide wire is then advanced from the femoral artery and navigated through the abdominal aorta AA, and to the renal artery RA. The guidewire may be visualized in the body using various means such as, for example, x-ray fluoroscopy and less commonly x-ray computed tomography (CT) and/or magnetic resonance imaging (MRI).

A standard delivery catheter 9 is advanced over the guidewire to access the lumen of RA, or otherwise along the guidewire until the distal end of the delivery catheter is in place in the renal artery and proximal to the region to be ablated. This catheter may also comprise a vascular sheath which effectively makes a channel for other catheters to be placed into the lumen of the renal artery.

The guidewire is then withdrawn.

A cryoablation probe is then advanced through the delivery catheter or sheath 9 until the cryoenergy delivery section 312 is positioned in the target location along the RA. The position of the cryoablation probe may be observed or confirmed using, for example, x-ray fluoroscopy. To this end, the probe may have marks tailored to the imaging methodology, such as radio opaque markers or rings seen by x-ray fluoroscopy.

The cryoprobe may be manipulated into the lumen of the RA, allowing blood to fill the gap between the wall and probe tip, or the probe may be manipulated, shaped, or deployed (e.g., curved or expanded) such that it contacts the wall of the RA directly.

The cryoprobe is then activated, extracting heat from the vessel wall, and cooling the renal nerve in its vicinity, causing disruption of the nerve function. The cryoprobe may be activated repeatedly with intervening active or passive thawing phases, similar to freeze:thaw:re-freeze cycles used for tumor ablation. The cryoprobe may be activated at different locations along the vessel. The cryoprobe may apply energy to the entire circumference of the lumen or to an arc less than 360 degrees, such as an arc corresponding to an angle of 270 degrees and sparing a 90 degree segment. Alternatively, a 90 degree ablation segment could be conceivable, for example corresponding to the 3 to 6 o'clock position. A gradient of ablation effect may thus be possible for the treating physician if total circumferential nerve ablation is not desired for the associated level of blood pressure response. Overtreatment of less severe levels of hypertension may thus also be avoided.

Temperature may be monitored (e.g., the temperature difference between the cryogen flowing into the distal tip region and the cryogen returning from the distal tip and correlated to a threshold energy delivery or tissue freeze at which point the cryoprobe is deactivated.

Finally, the probe is withdrawn from the vasculature.

The cryo-based ablation method for renal neuromodulation has a number of benefits over heat-based ablation technology including: 1) clear visualization of the ice by common imaging modalities (i.e., ultrasound, computed tomography, magnetic resonance imaging); 2) a much lower pain or procedure discomfort; and 3) improved healing of underlying and/or surrounding tissue due to preservation of the collagenous architecture which is used as a scaffold for inflammatory cells that auto digest the tissue of the ablation zone with minimal associated scar formation.

As will be discussed in greater detail herein, the cryoablation method and the cryoablation system and probe may vary widely.

Cryoablation System

A preferred cooling system for cryoablation treatment uses liquid refrigerants at low pressures and cryogenic temperatures to provide reliable cooling of the distal end of a cryoapparatus such as, for example, the cryoprobe or catheter mentioned above. The use of liquid refrigerants as the cooling means combined with a multitubular distal end of the cryoapparatus eliminates the need for refrigerant vaporization and significantly simplifies a cryoablation procedure.

Figure 2:
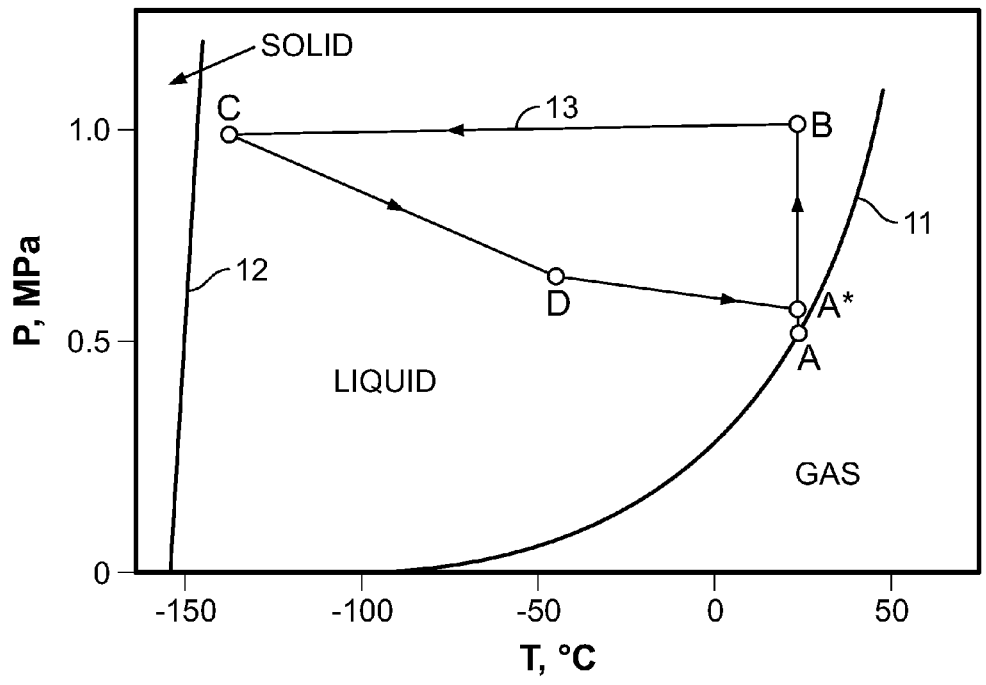
FIG. 2 is a phase diagram corresponding to a cooling cycle of a liquid refrigerant used in a cryoablation system.

An example of the use of low pressure and cryogenic temperature refrigerants is illustrated in FIG. 2. In particular, a phase diagram of R218 refrigerant (octafluoropropane) having a melting temperature of about −150° C. is shown. The axes of the diagram in FIG. 2 correspond to pressure P and temperature T of the R218 refrigerant, and include phase lines 11 and 12 that delineate the locus of points (P, T) where solid, liquid and gas states coexist. Although R218 is shown in connection with this embodiment, the invention may include use of other liquid refrigerants.

At point A of FIG. 2, the refrigerant is in a "liquid-vapor" equilibrium state in a storage tank or container. It has a temperature $T_0$ of the environment, or slightly lower, at an initial pressure $P_0$ of about 0.4 MPa. The closed loop cycle or refrigerant flowpath begins at the point where the liquid refrigerant exits the container or storage tank. In order for the refrigerant to remain in the liquid state throughout the entire cooling cycle and provide necessary pressure for the cryogen to flow through a cryoprobe or a catheter it is maintained at a slightly elevated pressure in the range from about 0.7 to 1.0 MPa (or in this example about 0.9 MPa). This corresponds to point B of FIG. 2. Point B is in the liquid area of R218 refrigerant. Further, the liquid is cooled by a cooling device (such as but not limited to a refrigerator) from point B to point C to a temperature $T_{min}$ that is shown by path 13 in FIG. 2. This temperature will be somewhat higher (warmer) than its freezing temperature at elevated pressure.

The cold liquid refrigerant at point C is used for cryoablation treatment and directed into the distal end of the cryodevice that is in thermal contact with the biological tissue to be treated. This thermal contact results in to a temperature increase of the liquid refrigerant with a simultaneous pressure drop from point C to point D caused by the hydraulic resistance (impedance) of the microchannel distal end of the cryoprobe. The temperature of the return liquid is increased due to its environment. In particular, the temperature is increased due to thermal communication with the ambient surroundings and by slightly elevated pressure maintained by a device, e.g., a check valve (point A*). A small pressure drop of about 6 kPa is desirable to maintain the liquid phase conditions in a return line that returns the liquid refrigerant back to the storage tank. Finally, the cycle or flowpath is completed at the point where the liquid cryogen enters the storage tank. Re-entry of the liquid refrigerant may be through a port or entry hole in the container corresponding once again to point A of FIG. 2. The above described cooling cycle may be continuously repeated as desired.

Refrigerators such as, for example, a Pulse Tube Refrigerator (PTR) having a temperature regulating device can be used to cool the liquid.

In some examples the cooling device or refrigerator can be a heat exchanger submerged in mildly pressurized liquid nitrogen having a predetermined temperature $T_{min}$ depending on its pressure. The pressure may range from about 1.0 to 3.0 MPa. The liquid nitrogen can be replaced by liquid argon or krypton. In these cases, the predetermined temperatures $T_{min}$ will be obtained at pressures as low as about 0.1 to 0.7 MPa.

Figure 3A:
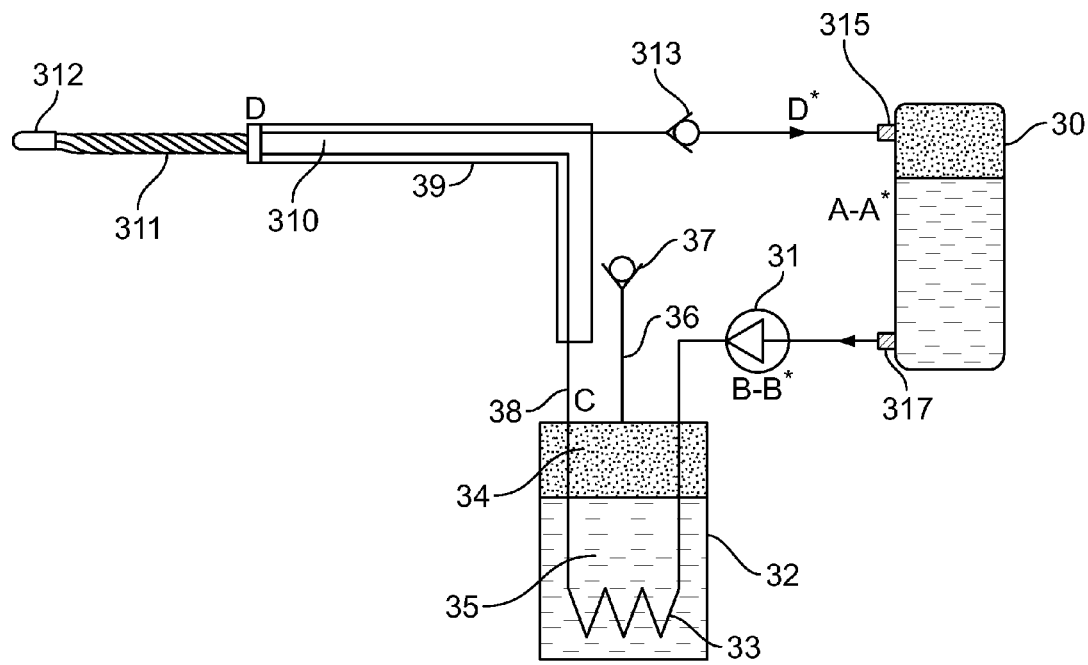
FIGS. 3A-3C are schematic representations of various types of cryoablation systems.

A cooling system for cryoablation treatment is schematically shown in FIG. 3A where the liquid refrigerant at initial pressure $P_0$ in container 30 is compressed by a liquid pump 31 under temperature $T_0$ of the environment. Contrary to typical closed cooling cycles where cooling is achieved by evaporating refrigerants followed by high compression of the vapor, this pump can be very small in size as it drives the incompressible liquid.

Further, the liquid refrigerant is transferred into the refrigerator 32 through the coiled portion 33 which is submerged in the boil-off cryogen 34, 35 provided by transfer line 36 and maintained under a predetermined pressure by check valve 37.

The boil-off cryogen has a predetermined temperature $T_{min}$. The coiled portion 33 of the refrigerator 32 is fluidly connected with multi-tubular inlet fluid transfer microtubes of the flexible distal end 311, so that the cold liquid refrigerant having the lowest operational temperature $T_{min}$ flows into the distal end 311 of the cryoprobe through cold input line 38 that is encapsulated by a vacuum shell 39 forming a vacuum space 310. The end cap 312 positioned at the ends of the fluid transfer microtubes provides fluid transfer from the inlet fluid transfer microtubes to the outlet fluid transfer microtubes containing the returned liquid refrigerant. The returned liquid refrigerant then passes through a check valve 313 intended to decrease the pressure of the returned refrigerant to slightly above the initial pressure $p_0$. Finally, the refrigerant re-enters the container 30 through a port or opening 315 completing the flowpath of the liquid refrigerant. The system provides continuous flow of a refrigerant, and the path A-B-C-D- A*-A in FIG. 3A corresponds to phase physical positions indicated in FIG. 2. The refrigerant maintains its liquid state along the entire flowpath or cycle from the point it leaves the container through opening 317 to the point it returns to the storage tank or container via opening 315.

An example of a closed loop cryoprobe using a liquid refrigerant is described in patent application Ser. No. 12/425, 938, filed Apr. 17, 2009, and entitled "Method and System for Cryoablation Treatment".

Preferably, the minimum achievable temperature $T_{min}$ of the described process is not to be lower than the freezing temperature of the liquid refrigerants to be used. For many practical applications in cryosurgery, the temperature of the distal end of the cryoprobe must be at least −100° C. or lower, and more preferably −140° C. or lower in order to perform a cryoablation procedure effectively. Non-limiting examples of non-toxic liquid refrigerants for use with the present invention are set forth in table 1 below. These have normal freezing temperatures at about −150° C. or lower.

TABLE 1

| Refrigerant | Chemical formula | Molecular mass (kg/mol) | Normal freezing point (° C.) |
|---|---|---|---|
| R218 | $C_3F_8$ | 188.02 | −153 |
| R124 | $C_2HClF_4$ | 136.5 | −199 |

TABLE 1-continued

| Refrigerant | Chemical formula | Molecular mass (kg/mol) | Normal freezing point (° C.) |
|---|---|---|---|
| R290 | $C_3H_8$ | 44.1 | −187 |
| R1270 | $C_3H_6$ | 42.08 | −185 |
| R600A | $i-C_4H_{10}$ | 58.12 | −160 |

Figure 3B:
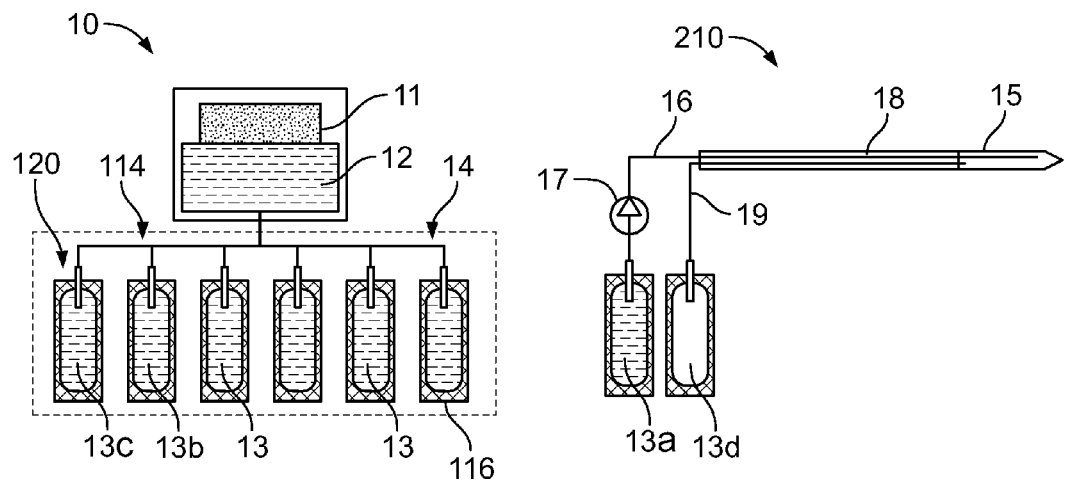
Figure 3C:
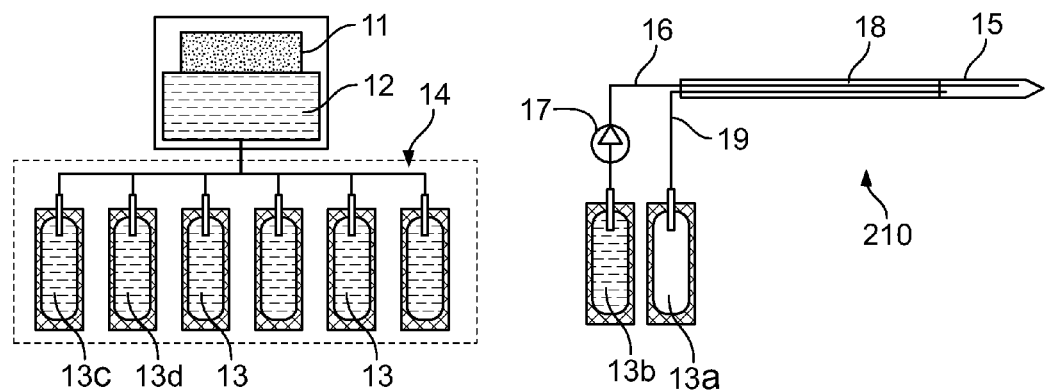

The cryogenic delivery container may also be designed as a hand held mini-container with a protective insulating shell as shown in FIGS. 3B-3C. Cryogenic containers may be arranged as several cartridges. For example, and with reference to FIG. 3B, the cold liquid refrigerant 12 may be delivered to the thermally insulated cryogenic containers 13b, 13c placed in docking station which may be in the form of a chamber 14. The containers are fluidly connected to the refrigerator via a refrigerator line 114. Each of the containers 13 has a connector 120 for detachably fluidly connecting to the refrigerator line 114. The line 114 in some instances may include two or more lumens to deliver fresh chilled liquid and remove warmer liquid. The line is connected to the container. An example of a connector is a fluid tight threaded nipple. However, other means of connectors may be used.

FIG. 3B also shows a container 13a, 13d installed in fluid communication with the cryoprobe 210. In particular, inlet line 16 of the cryoprobe is fluidly connected to container 13a. A liquid pump 17 is positioned along the refrigerant flowpath to pressurize the liquid refrigerant, driving the liquid refrigerant from the container 13a to the cryoprobe tip section 15. In other embodiments the pump can be placed in other locations within the 210 system. Return line 19 transports the liquid refrigerant from the distal section 15 towards the proximal end of the probe and ultimately to an empty receiver container 13d.

FIG. 3B also shows cryoprobe having an insulation 18. The insulation 18 surrounds the inlet line 16 and return line 19 to thermally insulate them from causing thermal damage to the surrounding healthy tissues. Insulation 18 may be in the form of a vacuum shell or another type of insulation such as a coating having a low coefficient of thermal conductivity.

The discharged cryogenic container 13a is disconnected from the inlet line 16 shown in FIG. 3B and connected to return line 19 of the cryoprobe 210 shown in FIG. 3C. Container 13d, which has been filled with warmer discharged liquid refrigerant from the cryoprobe is placed or docked in chamber 14. Newly charged cryogenic container 13b is then connected with inlet line 16 and becomes a cryogenic delivery container as shown in FIG. 3C.

In this manner, each of the containers 13a,b,c,d may be charged, spent (or used), refilled, and returned to the docking station in a convenient, interchangeable manner. The containers shown in this embodiment are identical in shape and size.

Further details of a SPLC system using a docking station and portable containers is described in U.S. patent application Ser. No. 12/770,572, filed Apr. 29, 2010.

Multi-Tube Cryoablation Probe

Figure 4A:
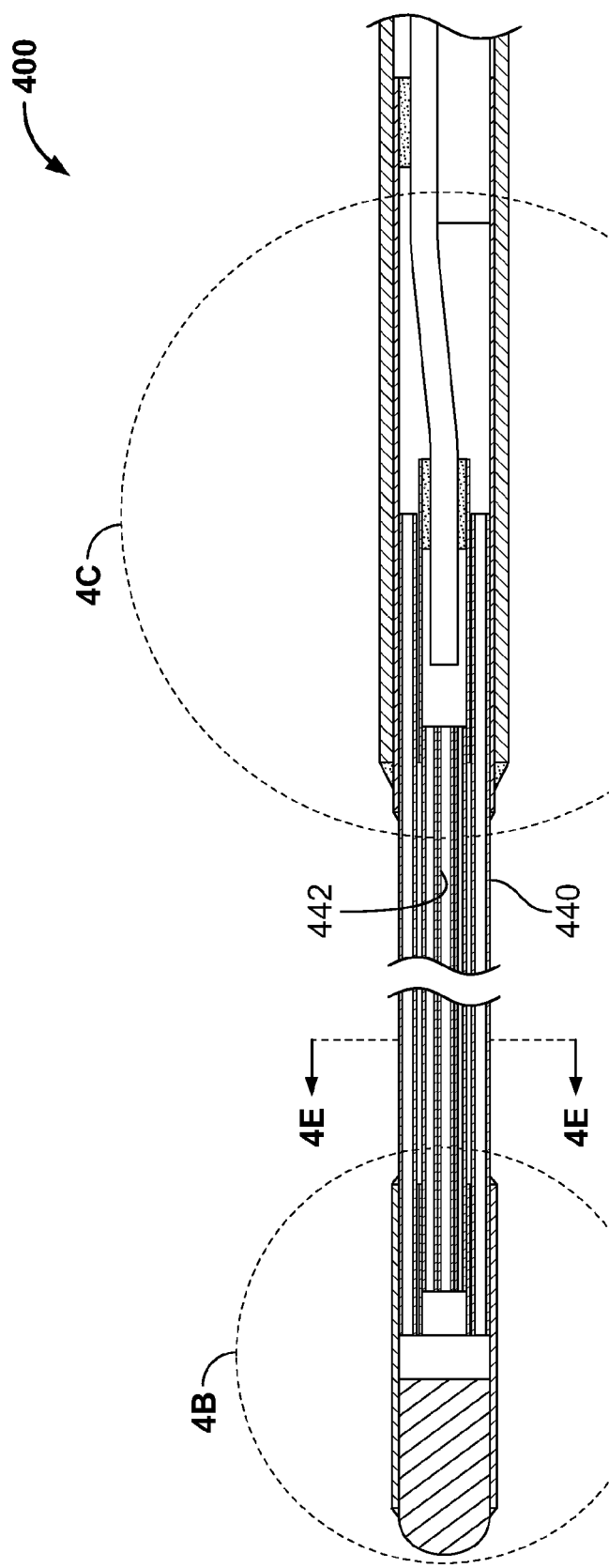
FIG. 4a is a cross sectional view of a distal section of a cryoprobe.

Referring to the FIG. 4a, a distal section 400 of a cryoprobe is shown. The distal section 400 includes a cryoenergy-delivery core section made up of a plurality of tubes 440, 442.

Figure 4B:
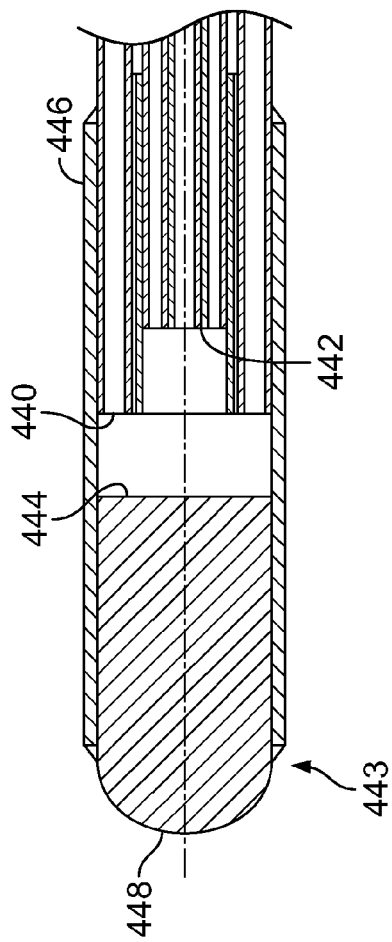
Figure 4C:
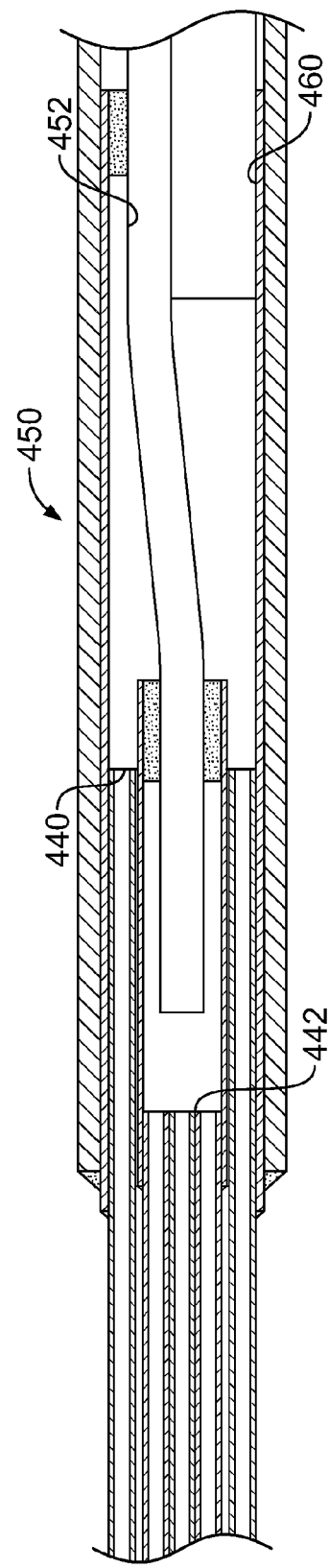

With reference to FIG. 4c and FIG. 4e, the distal section 400 includes two sets of tubes: inlet fluid transfer microtubes 440 and outlet fluid transfer microtubes 442. The inlet fluid transfer tubes 440 direct liquid refrigerant to the distal section of the cryoprobe creating a cryogenic energy delivering region (or core) to treat tissue in the vicinity of the probe. These cooling (or active) microtubes are shown in an annular formation. The outlet fluid transfer (or return) microtubes 442 direct liquid refrigerant away from the target site.

FIG. 4b is an enlarged view of the distal end of energy delivering section 400 shown in FIG. 4a. An end cap 443 is positioned at the ends of the inlet microtubes 440 and outlet microtubes 442, defining a fluid transition chamber 444. The transition chamber 444 provides a fluid tight connection between the inlet fluid transfer microtubes and the outlet fluid transfer microtubes. The end cap may be secured and fluidly sealed with an adhesive or glue. In one embodiment, a bushing 446 is used to attach plug 448 to the distal section. Other manufacturing techniques may be employed to make and interconnect the components and are still intended to be within the scope of the invention.

FIG. 4c illustrates an enlarged view of a transitional region 450 in which the plurality of cooling microtubes 440 are fluidly coupled to one or more larger inlet passageways 460 and the return microtubes are fluidly coupled to one or more larger return passageways 452. The return line(s) ultimately direct the liquid refrigerant back to the cryogen source or container such as, for example, container 30 described in FIG. 3A above, and thereby complete the flowpath or loop of the liquid cryogen and without allowing the cryogen to evaporate or escape.

The inlet line 460 may be thermally insulated. Insulation may be carried out with coatings, and layers formed of insulating materials. A preferred insulating configuration comprises providing an evacuated space, namely, a vacuum layer, surrounding the inlet line.

The fluid transfer microtubes may be formed of various materials. Suitable materials for rigid microtubes include annealed stainless steel. Suitable materials for flexible microtubes include but are not limited to polyimide (e.g., Kapton® polyimide from DuPont). Flexible, as used herein, is intended to refer to the ability of the multi-tubular distal end of the cryoprobe to be bent in the orientation desired by the user without applying excess force and without fracturing or resulting in significant performance degradation. This serves to manipulate the distal section of the cryoprobe about a curved tissue structure.

Flexible microtubes may be formed of a material that maintains flexibility in a full range of temperatures from −200° C. to ambient temperature. Materials may be selected that maintain flexibility in a range of temperature from −200° C. to 100° C. One example of such material is polyimide.

The dimensions of the fluid transfer microtubes may vary. Each of the fluid transfer microtubes preferably has an inner diameter in a range of between about 0.05 mm and 2.0 mm and more preferably between about 0.1 mm and 1 mm, and most preferably between about 0.2 mm and 0.5 mm Each fluid transfer microtube preferably has a wall thickness in a range of between about 0.01 mm and 0.3 mm and more preferably between about 0.02 mm and 0.1 mm Ice shapes may be formed about the multi-tubular distal end of cryoprobe. The ice shape can be created in a desired form by bending the distal end in the desired orientation including, e.g., a curve, arc, or complete loop. The flexible multitubular probe allows for complex bending motion including complete loops to be formed.

FIG. 4F illustrates a flexible multitubular catheter 400 in an application, namely, to cause severe cooling (e.g., <−40 C) within the artery wall 472 to modulate the renal nerve function. As shown in FIG. 4F, the catheter 400 is positioned in the renal artery 472 and cooling energy is delivered from the catheter 400. Application of the cooling energy causes occlusion of the renal artery (of average internal lumen diameter of ~6 mm) Ice 474 is formed and fills the remaining space. There is about a 4 mm diameter space around the catheter, the catheter itself having a diameter of about 2 mm The cryocatheter of this embodiment thus indirectly cools the renal artery wall, and associated renal nerve, via contacting the wall with a layer of ice. It is noted that while this may not be the ideal contact for maximal direct cooling effect, the power of the system described herein is sufficiently strong such that a balloon is unnecessary.

A 3D volumetric structure such as a hook, loop, or basket can support the microtubes. The structure can be actuated to change shape, expand, curve, etc. Techniques for changing the shape include, without limitation, pull wires, self expanding materials, shape memory materials, and inflatable balloons as will be described herein. The flexible microtubes may thus be selectively urged into a deployed configuration with more direct contact with the inner vessel wall for optimal transfer of the cold into the wall. The tubes may be expanded radially and circumferentially by the basket or expandable structure.

Further details of a cryoablation multitubular probe are described in U.S. patent application Ser. No. 12/754,457, filed Apr. 4, 2010.

Cryoablation Balloon Catheter

Figure 5A:
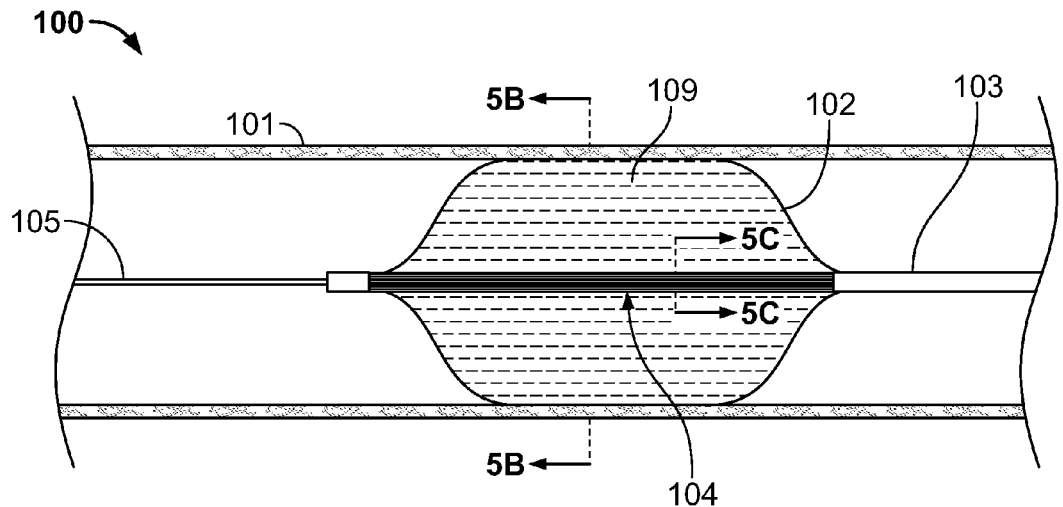
FIG. 5A is an illustration of a cryoablation balloon catheter inside a lumen.

With reference to FIGS. 5A, a cryoablation balloon catheter 100 is shown in a lumen 101 such as a blood vessel, airway, or other tubular organ. In a method, catheter may be advanced to a particular location along the lumen via manipulating the proximal end of the catheter as is known to those of ordinary skill in the art. For example, as described above, the catheter may be advanced through a catheter sheath.

Figure 5B:
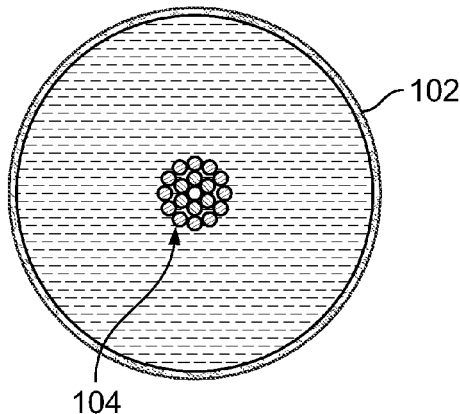
FIG. 5B is a cross sectional view corresponding to the plane 5B-5B of the inflated balloon of the catheter shown in FIG. 5A.
Figure 5C:
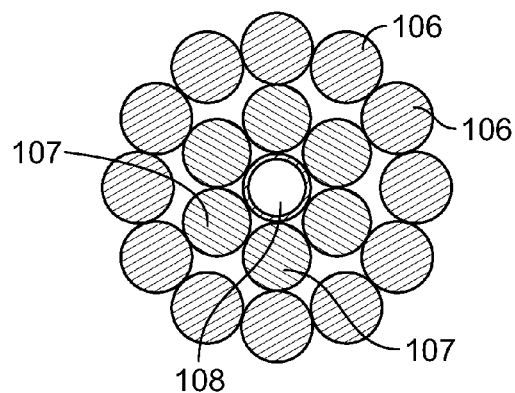
FIG. 5C is a cross sectional view corresponding to the plane 5C-5C of the inflated balloon of the catheter shown in FIG. 5A.

Alternatively, balloon catheter or probe may be advanced directly over the guidewire without the need for a delivery sheath. In particular, and as shown in FIG. 5A, catheter 100 is disposed over a guidewire 105. A guidewire lumen 108 as shown in FIG. 5C is sized to slideably receive a guidewire. However, it is to be understood that the invention is not so limited as to require a guidewire except where explicitly recited in the claims.

As shown in FIG. 5A, the distal section of the catheter comprises a balloon 102. The balloon 102 encases or surrounds one or more cryotubes 104. Preferably, balloon catheter 100 includes a plurality of delivery tubes 106 and return tubes 107 in a concentric arrangement as shown in FIG. 5B, 5C. The delivery tubes 106 are shown on the outer perimeter of bundle 104, concentrically surrounding, return tubes 107. Though the microtubes are shown in a particular arrangement, their order or arrangement may vary. For example the microtubes may also be disposed in a weave, braid, or twisted bundle.

Figure 5D:
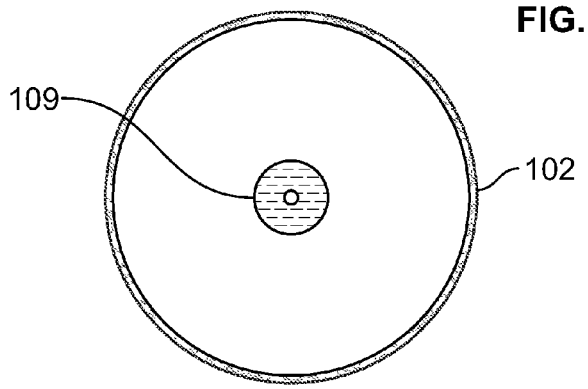
FIG. 5D is a cross sectional view of an alternative balloon catheter design taken along 5B-5B.

FIG. 5D shows another balloon catheter design and in particular, a cryoenergy core having only one lumen for delivering the cryogen to the tip, and one return lumen for returning the cryogen. The balloon catheter, although not shown, may also have a guide wire channel 108 similar to that shown in FIG. 5C.

The balloon may be attached to the distal section of the catheter using adhesive, heat, or another technique. In one embodiment, a bushing is used to attach balloon to the distal section. Other manufacturing techniques may be employed to make and interconnect the components and are still intended to be within the scope of the invention.

Balloon or sheath 102 may be inflated with a fluid 109 such as a thermally conducting liquid, gel, superfluid, gas, or metal that does not exceed the upper pressure limit of balloon catheters. Examples of thermally conducting liquids include but are not limited to water and a non-toxic salt solution such as, e.g., saline at 0.9% sodium chloride.

A fluid inflation lumen extending through the catheter includes at least one distal port in fluid communication with the balloon. The fluid inflation lumen also includes a proximal port for receiving the fluid. For example, a proximal port of the fluid inflation lumen may be connected to a syringe, pump or another fluid source (not shown) via a Luer lock to deflate (reduce) and inflate (expand) the balloon or sheath with a thermally conductive liquid.

Figure 6A:
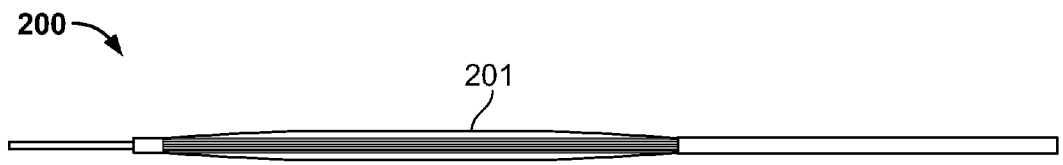
FIG. 6A is an illustration of a deflated balloon 201 that is folded for insertion into a blood vessel.
Figure 6B:
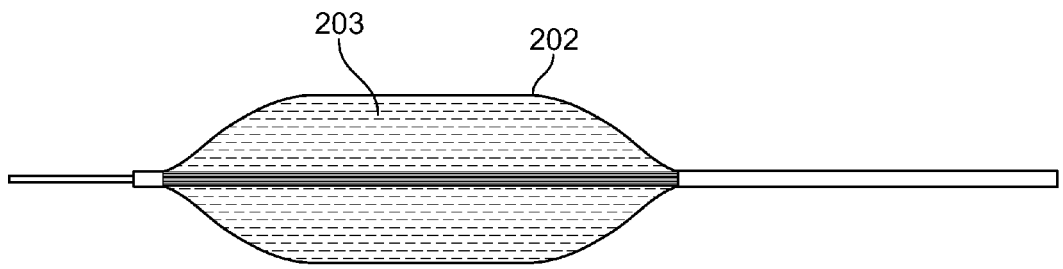
FIG. 6B is an illustration of an inflated balloon 202 with a thermally conductive liquid 203 inside.

Once the balloon catheter is fully inflated as shown for example in FIGS. 5A, and 6B, the SPLCS may run refrigerant though the multi-tubes 104. Cooling is achieved by circulating SPLC with its in initial temperature below −90 C through the multitubular section 104 that is in good thermal contact with the thermally conductive liquid 109, 203 that fills the balloon. Without being bound to theory, it is noted that the cryoablation balloon catheter transfers heat differently than the cryoprobe described in connection with FIG. 4 above. In particular, instead of directly extracting heat from the tissue as described above in connection with the cryoprobe shown in FIG. 4, the cryoablation balloon catheter of FIG. 5 transfers or extracts heat from the medium 109 used to inflate the balloon part of the catheter. The entire surface of the balloon catheter serves to extract heat from the tissue, and freeze the renal sympathetic nerve.

Additionally, use of the balloon catheter described herein can have the benefit of remodeling the renal artery lumen if stenosis has occurred. See also International Application No. PCT/US11/49287, filed Aug. 26, 2011, entitled "Cryoablation Catheter and Method" for further details regarding cryoablation balloons.

Figure 7A:
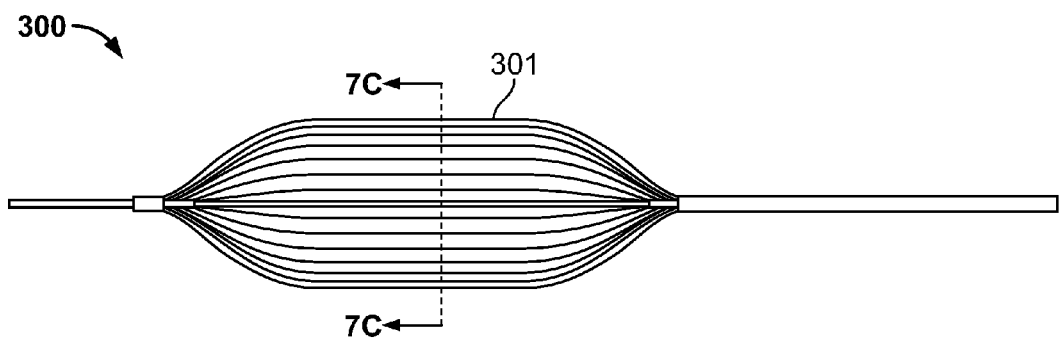
FIG. 7A is an illustration of an inflated balloon with plurality of small tubes adhered to its surface.
Figure 7B:
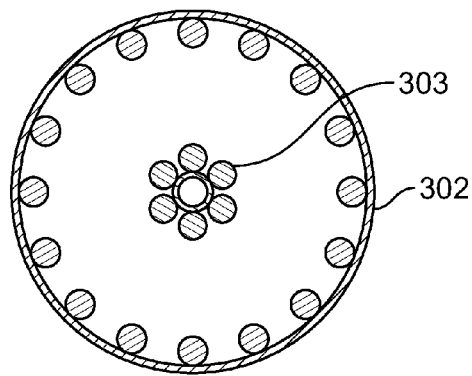
FIG. 7B is a cross sectional view of the balloon of FIG. 7A with the tubes 301 conducting the incoming flow of SPLC placed on the inner surface of the balloon 302 with the return flow of the SPLC going through the central part of the balloon 303.
Figure 7C:
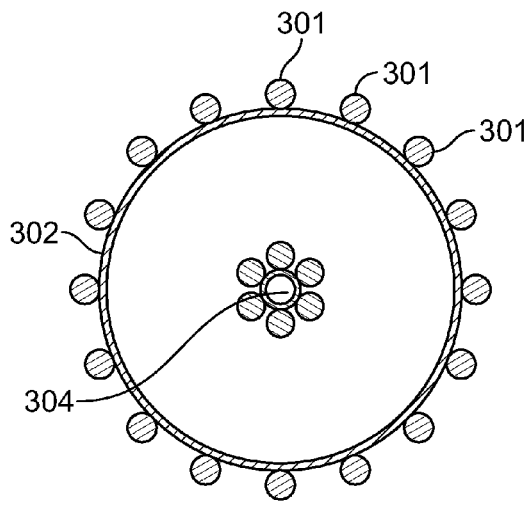
FIG. 7C is a cross sectional view of the balloon with the tubes 301 conducting the incoming flow of SPLC placed on the outside surface of the balloon 302 with the return flow of the SPLC going through the central part of the balloon 303.

FIGS. 7A-7C show another cryoablation balloon catheter 300 having microtubes 301, 303 that have refrigerant (preferably SPLC) flowing through them. However, unlike the embodiment shown in FIGS. 5-6 above, the microtubes are shown disposed (e.g., adhered) to the inside (FIG. 7B) or outside (FIG. 7C) of the balloon catheter wall 302.

The micro-tubes are preferably evenly dispersed around the perimeter or circumference of the balloon. The number of microtubes disposed around the balloon may vary widely. In one embodiment, as shown in FIG. 7C, 10-20 and more preferably 15- 20 microtubes are present. In another embodiment, the number microtubes is sufficient such that a continuous layer of tubing is formed around the exterior of the outer balloon surface.

In one embodiment of the invention, individual microtubes may be selectively activated such that a specific arcuate region of the balloon or probe is activated. Consequently, when the balloon or tubular structure is placed against the wall of the lumen, a specific arcuate region spanning less than or equal to 360 degrees may be treated. Variable circumferential regions may be treated in different arteries or within the same artery to better gauge the final physiologic intensity of the blood pressure response.

Figure 7D:
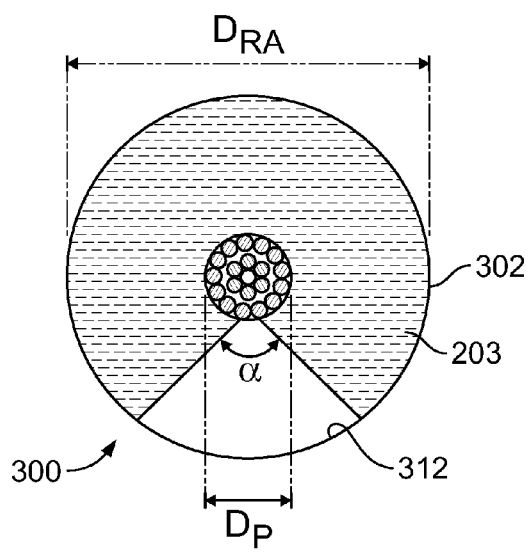
FIG. 7D is a cross section of a multi-chamber cryoablation balloon catheter.

In another embodiment, and with reference to FIG. 7D, a two chamber balloon has a first chamber filled with a conducting medium 203 as described above, and a second chamber filled with an insulating medium 312 such as naturally insulating air, etc. The insulating medium 312 may span an arc equal to an angle (alpha) which may range from 40 to 80 degrees or about 60 degrees.

Catheter and balloon sizes may vary widely. One embodiment of the invention includes a 2 mm catheter inside an 8 mm 2-chamber balloon. However, the balloon may include multiple chambers to hold the insulating medium 312 corresponding to multiple untreated regions along the lumen. In another embodiment, 3-6 insulating chambers are provided in the balloon. Flow may be controlled variously. One embodiment includes placing independently controlled valves or switches to provide flow to the microtubes. The valves may be connected to a controller or computer to receive operating instructions.

Figure 8A:
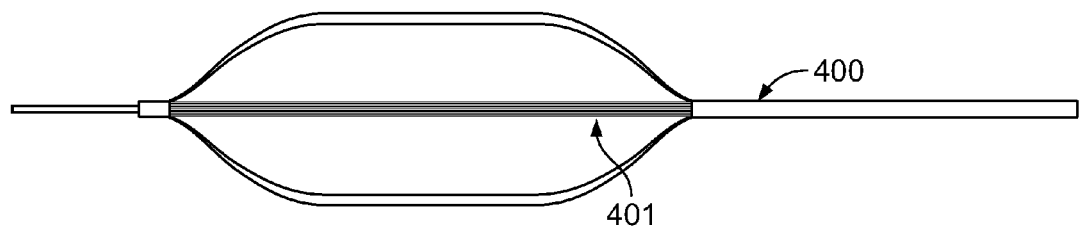
FIG. 8A is an illustration of a double balloon cryoablation balloon catheter with a multitubular cooling section inside the inner balloon.

FIG. 8A is an illustration of a double balloon cryoablation balloon catheter 400 having a multitubular inner energy delivering core 401. The energy delivering core 401 comprises one or more microtubes as described above in connection with the multitubular designs of FIG. 5.

Figure 8B:
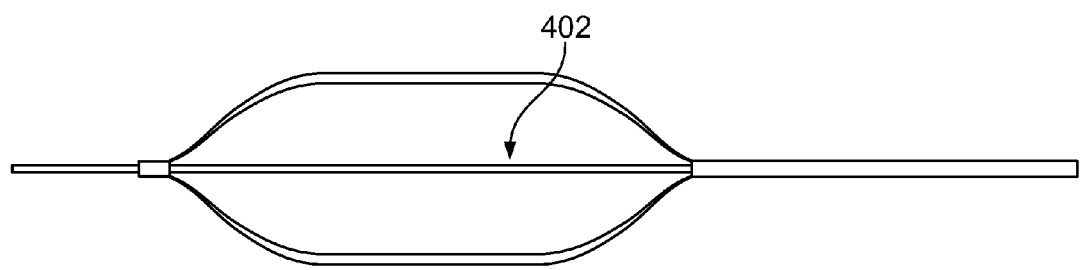
FIG. 8B is an illustration of a double balloon cryoablation balloon catheter cooled directly by SPLC 402 circulating inside the balloon.

FIG. 8B is an illustration of another double balloon cryoablation balloon catheter. However, unlike the embodiment of FIG. 8A and the use of an energy delivering core to cool a thermally conductive liquid within the balloon, the balloon is filled directly with a single phase, liquid cryogen.

Such a system may comprise a container for holding the liquid refrigerant at an initial pressure and initial temperature; a liquid pump; and the cryoablation double balloon catheter coupled to the container.

A fluid delivery lumen and a fluid return lumen extending through the elongate shaft and to the balloon members can be provided such that the balloon member is in fluid communication with the liquid refrigerant.

The balloon catheter is adapted to be expanded when liquid refrigerant is sent into the balloon member, and to be reduced in size when liquid refrigerant is withdrawn from the balloon member. Preferably the return lumen is fluidly coupled to a second container thereby completing the loop of the liquid refrigerant without the liquid refrigerant evaporating as the refrigerant is transported. In one embodiment of the invention, the containers are hand held or portable. In another embodiment, the shaft is stiff.

The double balloon may be expanded in various shapes. An example of one shape is shown in FIG. 8B.

Figure 9A:
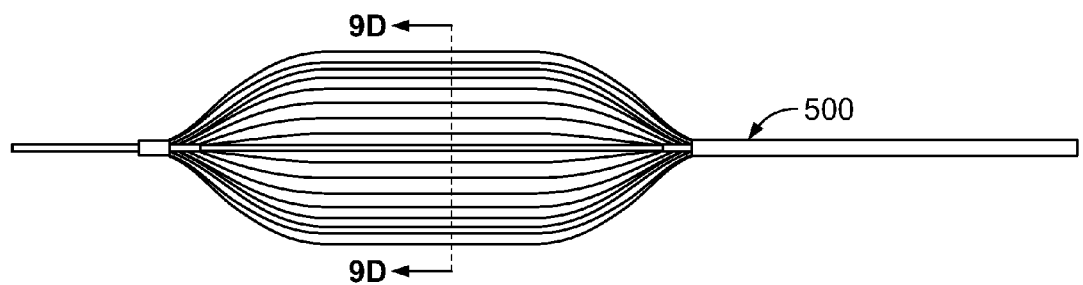
FIGS. 9A-9D are illustrations of a double balloon cryoablation balloon catheter with plurality of cooling lines adhered to the balloon walls in different configurations.
Figure 9B:
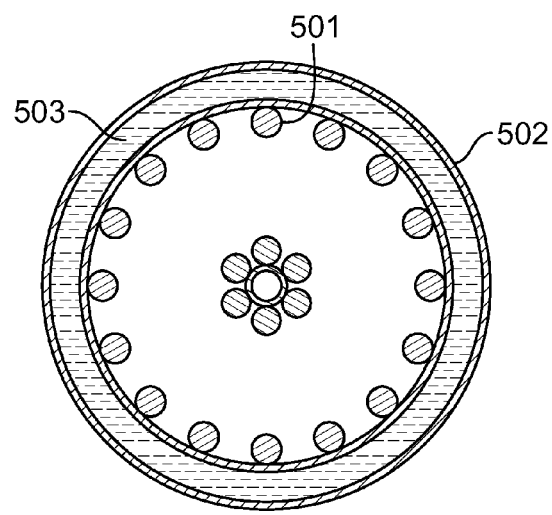
Figure 9C:
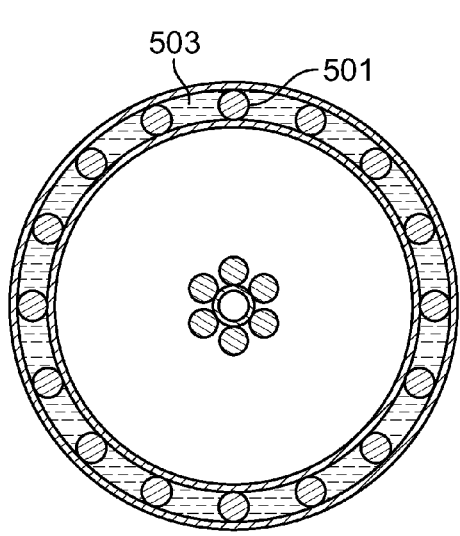
Figure 9D:
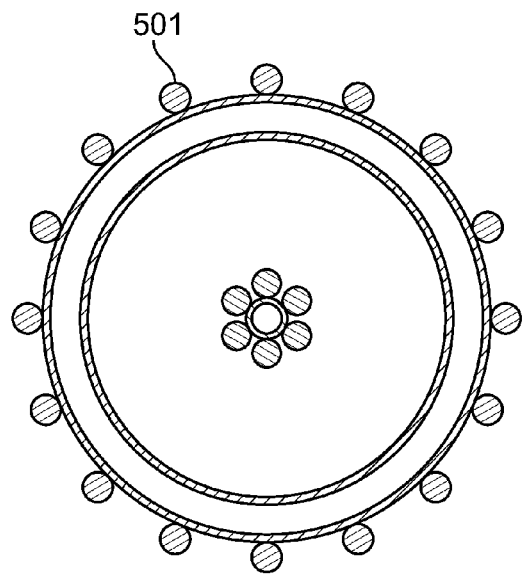

FIGS. 9A-9D show another cryoablation balloon catheter comprising two or more sheath layers. Thermal delivery micro-tubes 501 are shown disposed inside the first or inner balloon 501 (FIG. 9B) or between the walls of the first balloon 501 and the second balloon 502 (FIG. 9C). A thermally conducting liquid 503 is preferably disposed in a gap between the balloon layers. Additionally, the thermal delivery microtubes 501 may be disposed on the outside of the second or outer balloon member 502 (FIG. 9D). Consequently, when the balloon catheter is inflated, the micro-tubules will be pressed against the tissue directly, or with only the wall of the balloon catheter obstructing direct contact, thereby increasing cooling efficiency.

Figure 10:
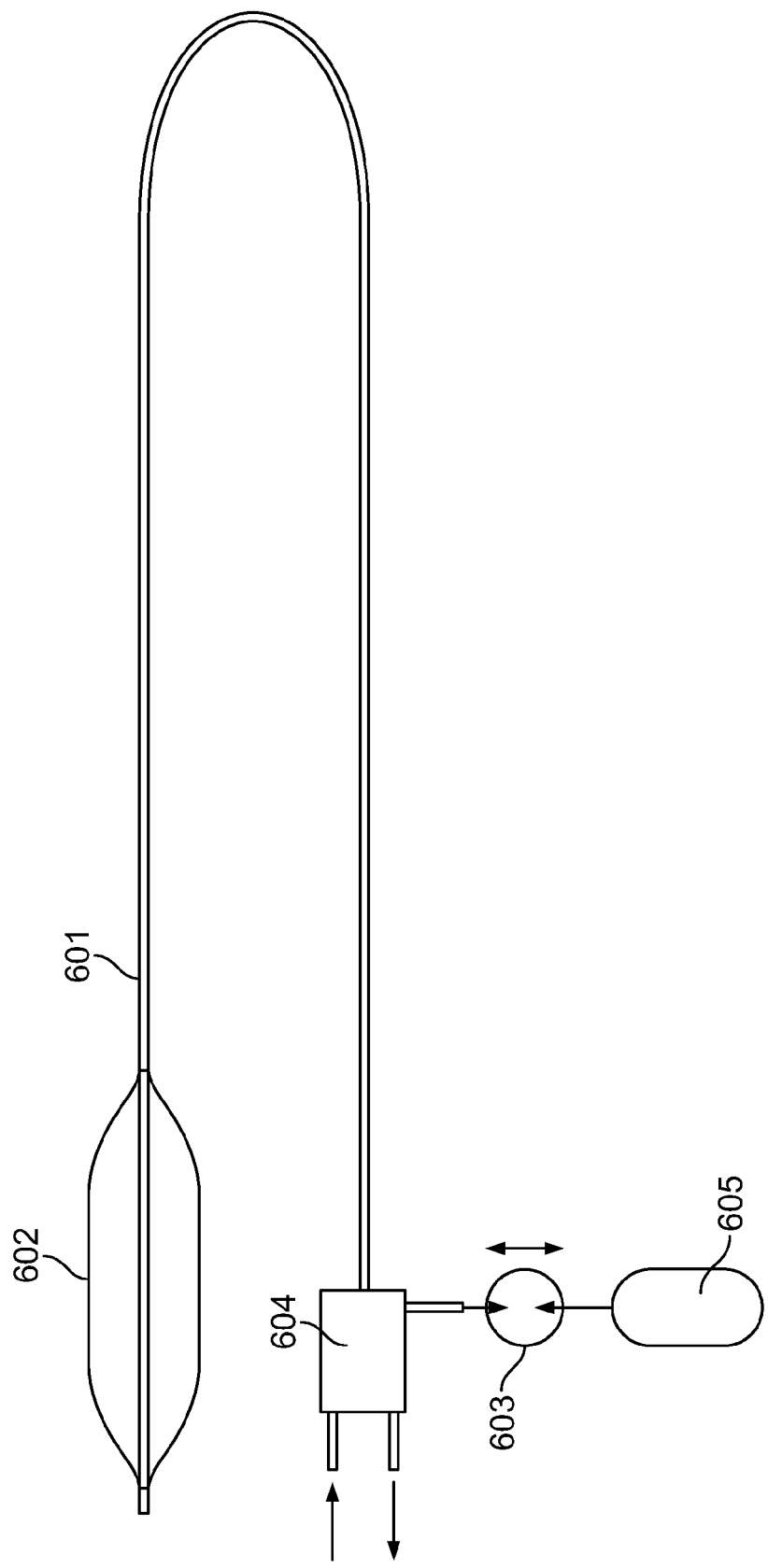
FIG. 10 is an illustration of a balloon catheter inflation system using a SPLC medium for the inflation medium.

FIG. 10 shows an inflation system of a balloon catheter 601. Inflation of the balloon is achieved by pumping a thermally conductive liquid inside the balloon 602 using a small liquid pump 603 (or syringe) attached to a designated balloon-inflation line in a connector 604. The thermally conductive liquid may be stored inside a container 605 at ambient temperature and pressure. To deflate the balloon 602, the liquid pump 603 is reversed.

The SPLC is circulated to a cryo-energy delivering core within the balloon 602 as described above. The SPLC is delivered and returned through, e.g., designated cryogen lines of connector 604.

The balloon may be made from a material that can withstand a temperature range of −200° C. to +100° C. Additionally, the balloon may be made from a material that can withstand a pressure up to 500 psi. A non-limiting example material is polyimide (Kapton® from DuPont).

Also, although the shape of the cryoablation balloon catheter 100 is shown as substantially elongate or cylindrical, and tapered, its dimensions and shape may vary greatly and as discussed further below, may be adapted for a particular application or treatment.

Figure 11A:
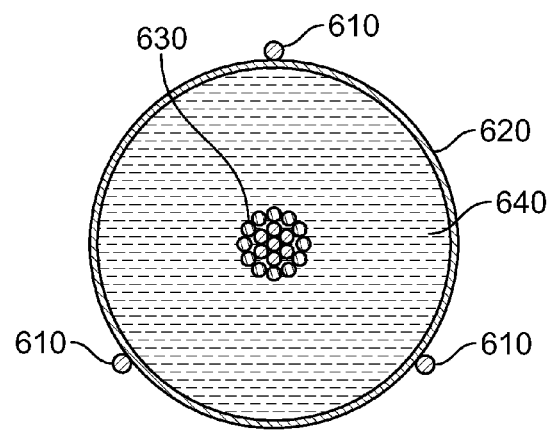
FIG. 11A is a cross section of a cryoablation balloon catheter having thermocouples on the exterior of the balloon for measuring temperature.

FIG. 11A shows cryoablation balloon setup for testing various thermally conductive liquids 640 and/or internal configurations of noted microtubules. The shown setup included a 7 mm diameter polyimide balloon 620 that has a 2.2 mm multitubular cryoprobe inside 630.

Three thermocouples 610 were attached to the outer surface of the balloon to measure its temperature as a function of time. The inner space of the balloon was filled with a thermally conductive liquid 640. The inflated balloon was then immersed in a room temperature ultrasound gel.

Figure 11B:
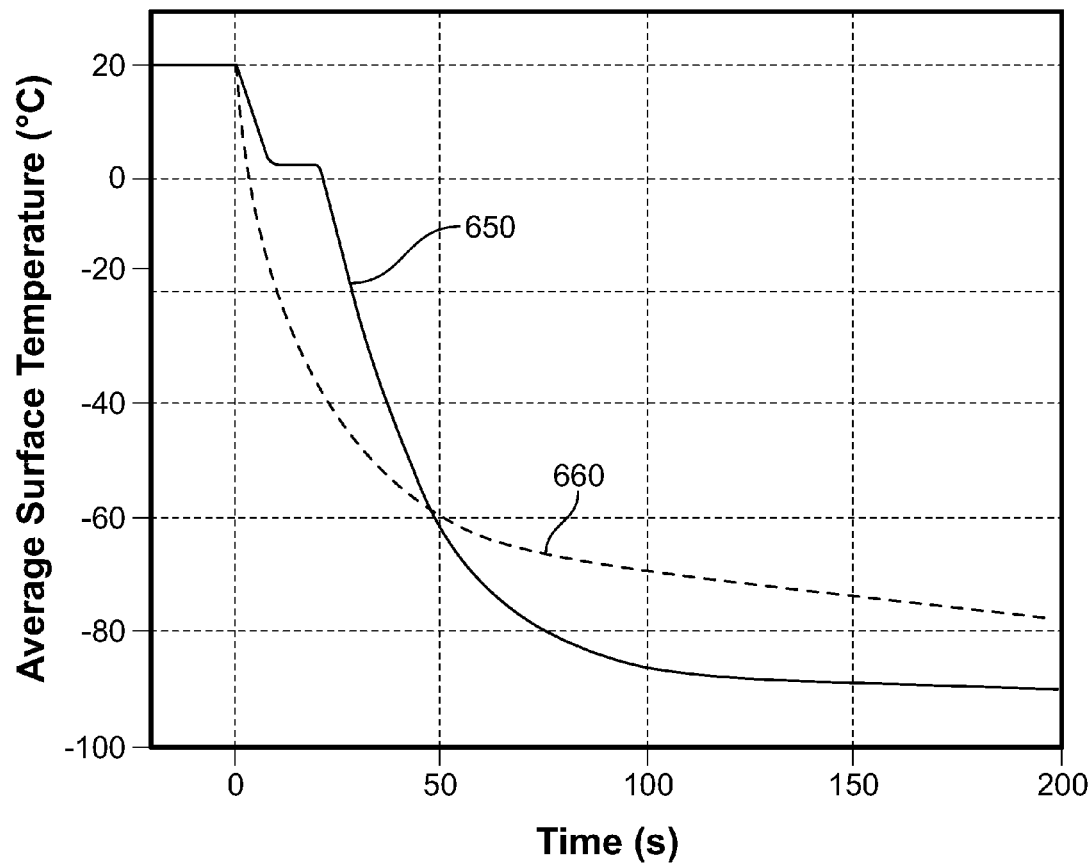
FIG. 11B is a plot indicating the temperature versus time for the balloon catheter shown in FIG. 11A for various thermally conductive mediums.

A plot is shown in FIG. 11B representing the average surface temperature (average of the three thermocouples readings) of the balloon when filled with water 660 and Gallium-Indium eutectic alloy 650 that is a liquid metal at room temperature. One can see that the liquid metal allows for faster and quicker cooling (ablation time) because after 50 seconds, the Gallium-Indium alloy continues to drop in temperature until about −90 degrees C. (about 20 degrees lower than the water 650).

Temperature Feedback

In some embodiments, methods and apparatus for real-time monitoring of an extent or degree of neuromodulation or denervation (e.g., an extent or degree of thermal damage) in the target neural fibers and/or of thermal damage in the non-target tissue may be provided. Likewise, real-time monitoring of the thermal energy delivery element may be provided. Such methods and apparatus may, for example, comprise a thermocouple or other temperature sensor for measuring the temperature of the monitored tissue or of the thermal energy delivery element. Power or total energy delivered additionally or alternatively may be monitored.

The temperature difference of the liquid cryogen at a location in the outgoing flow and a location in the incoming flow may be monitored. This temperature difference may be correlated with tissue freeze, power delivery, cryoenergy delivery, etc. Once a temperature difference threshold is hit, the probe may be deactivated. Temperature may be further controlled by supplying a heated liquid or fluid through the probe. This system may also be used as a heating device by gently warming the circulating liquid, which may be used to thaw the surrounding ice within the artery lumen in a multiple freeze cycle format as previously described. Alternatively, it could be heated above 40 degrees C. to purposely thrombosis the artery such as the renal artery to embolize the entire kidney or help mitigate bleeding. One such cryoablation system is shown and described in patent application Ser. No. 12/754,457, filed Apr. 5, 2010. See also patent application Ser. No. 12/643,919, filed Dec. 21, 2009.

The above described methods and apparatuses have a wide variety of diagnostic and therapeutic applications including but not limited to external and internal cardiac applications, endoscopic applications, laparoscopic applications, surgical tools, endovascular uses, subcutaneous and superficial dermatologic applications, radiological applications, and others.

An endovascular method for treating hypertension includes use of a cryoablation catheter, with or without a surrounding balloon to denervate the renal artery. The distal section of the balloon catheter is advanced from a peripheral artery through the aorta into the renal artery, preferably starting in the femoral artery in the groin or the brachial artery in the arm. The exposed cold segment of the bare multifilament catheter or balloon is activated or inflated with cold liquid which penetrates the wall of the artery and ablates/kills the nerves within and/or surrounding the wall of the artery. Cold temperatures of between −20° C. to −150° C. are applied by the catheter in either single or multiple freeze/inflation cycles to produce long-lasting the nerve destruction/non-function.

A laparoscopic method for treating hypertension includes a cryoablation probe to denervate the renal artery. The distal section of the cryoprobe is advanced through the abdomen to access the renal hilum. The probe is placed in the vicinity of the renal nerve and/or in direct contact with the wall of the renal artery. The probe may be curved or otherwise shaped around the artery to ablate a region along the artery. The region treated may span an arc ranging up to 360 degrees.

Cryo-induced renal neuromodulation, whether delivered in an open procedure, extravascularly, intravascularly, intra-to-extravascularly or a combination thereof, may lower BP, alleviate clinical symptoms of Chronic heart failure (CHF), hypertension, diabetes, and their potential interacting metabolic combinations, such as those associated with polycystic ovary syndrome. Alternatively, as symptoms reoccur, or at regularly scheduled intervals, the patient may receive repeat therapy.

Although preferred illustrative variations of the present invention are described above, it will be apparent to those skilled in the art that various changes and modifications may be made thereto without departing from the invention. It is intended in the appended claims to cover all such changes and modifications that fall within the true spirit and scope of the invention.

REFERENCES

1. Krum H, Schlaich M, Whitbourn R, Sobotka P A, Sadowski J, Bartus K, Kapelak B, Walton A, Sievert H, Thambar S, Abraham W T, Esler M. Catheter-based renal sympathetic denervation for resistant hypertension: a multicentre safety and proof-of-principle cohort study. Lancet. 2009; 11; 373: 1275-81.

2. Katholi R E, Rocha-Singh K J. The role of renal sympathetic nerves in hypertension: has percutaneous renal denervation refocused attention on their clinical significance? Prog Cardiovasc Dis. 2009; 52:243-8.

3. Dibona G F, Esler MD. Translational Medicine: the antihypertensive effect of renal denervation. Am J Physiol Regul Integr Comp Physiol. 2009 Dec. 2. [Epub ahead of print]

4. Symplicity HTN-2 Investigators, Esler M D, Krum H, Sobotka P A, Schlaich M P, Schmieder R E, Böhm M. Renal sympathetic denervation in patients with treatment-resistant hypertension (The Symplicity HTN-2 Trial): a randomised controlled trial. Lancet. 2010; 376:1903-9.

5. Ukena C, Mahfoud F, Kindermann I, Barth C, Lenski M, Kindermann M, Brandt M C, Hoppe U C, Krum H, Esler M, Sobotka P A, Bohm M. Cardiorespiratory response to exercise after renal sympathetic denervation in patients with resistant hypertension. J Am Coll Cardiol 2011; 58:1176-82.

6. Mahfoud F, Schlaich M, Kindermann I, Ukena C, Cremers B, Brandt M C, Hoppe U C, Vonend O, Rump L C, Sobotka P A, Krum H, Esler M, Böhm M. Effect of renal sympathetic denervation on glucose metabolism in patients with resistant hypertension: a pilot study. Circulation 2011; 123:1940-6. Epub 2011 Apr. 25.

7. Symplicity HTN-1 Investigators. Catheter-based renal sympathetic denervation for resistant hypertension: durability of blood pressure reduction out to 24 months. Hypertension. 2011; 57:911-7. Epub 2011 Mar. 14.

8. Schlaich M P, Krum H, Sobotka P A, Esler M D. Renal denervation and hypertension. Am J Hypertens. 2011; 24:635-42

9. Schlaich M P, Straznicky N, Grima M, Ika-Sari C, Dawood T, Mahfoud F, Lambert E, Chopra R, Socratous F, Hennebry S, Eikelis N, Bohm M, Krum H, Lambert G, Esler M D, Sobotka P A. Renal denervation: a potential new treatment modality for polycystic ovary syndrome? J Hypertens. 2011; 29:991-6.

10. Tanguay J F, Geoffroy P, Dorval J F, Sirois M G. Percutaneous endoluminal arterial cryoenergy improves vascular remodelling after angioplasty. Thromb Haemost. 2004; 92:1114-21.

11. Dorval J F, Geoffroy P, Sirois M G, Tanguay J F. Endovascular cryotherapy accentuates the accumulation of the fibrillar collagen types I and III after percutaneous transluminal angioplasty in pigs. J Endovasc Ther 2006; 13:104-110.

We claim:

1. A method for renal nerve modulation comprising the steps of: navigating a distal cryoenergy delivery section of a cryoablation catheter through the vasculature and into the renal artery to a first location in proximity of the renal nerve; and ablating the renal nerve by applying cryoenergy from said distal cryoenergy delivery section of the cryoablation catheter to decrease the temperature of the renal artery to a first temperature such that nerve function is impaired, wherein the first temperature is less than or equal to −20 ° C., and wherein the applying cryoenergy from the distal cryoenergy delivery section comprises pumping a liquid cryogen along a flowpath to and from the distal region of the catheter and maintaining the cryogen in a liquid-only state without changing to a gaseous phase.

2. The method as recited in claim 1 wherein applying cryoenergy from the distal cryoenergy delivery section comprises pumping a cryogen through a plurality of flexible active microtubes and return microtubes.

3. The method as recited in claim 2 wherein the plurality of active microtubes are exteriorly disposed on a surface of an expandable balloon.

4. The method as recited in claim 1 further comprising positioning the distal cryoenergy delivery section in contact with a wall of the renal artery.

5. The method as recited in claim 4 wherein the distal cryoenergy delivery section is positioned in contact with the wall by expanding a balloon member.

6. The method as recited in claim 5 wherein expanding the balloon member comprises inflating the balloon member to a pressure of at least 100 psi.

7. The method as recited in claim 1 wherein the distal cryoenergy delivery section is positioned in the renal artery and spaced from the wall of the artery, and wherein said ablating step includes creating ice around the distal energy delivery section of the cryoablation catheter to temporarily occlude the renal artery and to create greater thermal conductivity to the renal artery wall.

8. The method as recited in claim 1 wherein said first temperature is less than or equal to −40° C.

9. The method as recited in claim 1 wherein said first temperature is less than or equal to −60° C.

10. The method as recited in claim 1 wherein the cryoenergy is applied to decrease the temperature of the renal artery to the first temperature for a first time period in the range of 15 to 200 seconds.

11. The method as recited in claim 10 wherein the first time period is in the range from 5 to 60 seconds.

12. The method as recited in claim 11 further comprising deactivating the applying cryo energy between the first time period and the second time period for a deactivation time period of at least 5 seconds.

13. The method as recited in claim 10, further comprising applying cryoenergy for a second time period.

14. The method as recited in claim 1 further comprising thawing ice surrounding the distal cryoenergy delivering section of the catheter 15. The method as recited in claim 14 wherein the step of thawing comprises warming the cryogen.

16. The method of claim 15 wherein the step of warming is performed between freezes, and at the conclusion of the procedure, and comprises transporting warmed cryogen in a liquid only state along the flowpath.

17. The method as recited in claim 13 wherein said second time period is in the range of 15 to 200 seconds.

18. The method as recited in claim 13 further comprising applying cryoenergy for a third time period, and wherein said third time period is in the range of 15 to 200 seconds.

19. The method as recited in claim 13 further comprising deactivating the applying cryo energy between the first time period and the second time period sufficient to allow the tissue to partially thaw.

20. The method as recited in claim 1 further comprising monitoring a real-time temperature difference between a liquid cryogen flowing towards the distal cryoenergy delivery section and the liquid cryogen returning from the distal cryoenergy delivery section.

21. The method as recited in claim 20 further comprising stopping the step of ablating when the real-time temperature difference over time is less than a threshold value.

22. The method as recited in claim 1 further comprising positioning the distal cryoenergy delivery section at a second location along the renal artery and in the vicinity of the renal nerve and repeating the ablating step at the second location.

23. A method for treating the renal nerve with cryoenergy comprising the steps of: navigating a distal cryoenergy delivery section of a cryoablation catheter through the vasculature and into the renal artery to a first location in proximity of the renal nerve; contacting the wall of the renal artery with the distal cryoenergy delivery section; and cooling the wall of the renal artery to a first temperature such that nerve function is disrupted wherein the step of cooling is carried out by transporting a cryogen in a liquid only state to and from the distal cryoenergy delivery section, and without changing to a gaseous phase subsequent to cooling the wall of the renal artery.

24. The method as recited in claim 23 wherein the contacting step is carried out by expanding an expandable structure associated with the distal cryoenergy delivery section.

25. The method as recited in claim 24 wherein the contacting step is carried out by expanding a balloon.

26. The method as recited in claim 25 wherein the cryogen is transported via a plurality of microtubes disposed inside of the balloon.

27. The method as recited in claim 24 wherein the contacting step is carried out by manipulation of a pull wire.

28. The method as recited in claim 24 wherein the expanding is performed by radially expanding the expandable structure.

29. The method as recited in claim 23 wherein the cooling step is performed by cooling an entire circumferential portion of the renal artery wall.

30. The method as recited in claim 23 wherein the cooling step is performed by cooling a portion of the renal artery wall corresponding to an arcuate segment between 90 and 270 degrees.

31. The method as recited in claim 23 wherein the renal artery wall is cooled to a depth of at least 2 mm to a first temperature less than $-40°$ C.

32. The method as recited in claim 23 wherein the first location is performed in a first trunk of the renal artery and the method further comprises moving the distal cryoenergy delivering section to a second location in a second trunk of the renal artery and cooling the renal artery at the second location.

33. The method as recited in claim 23 wherein the renal artery is within a patient having a vascular metal stent in an artery selected from the group consisting of coronary, major, and peripheral arteries.

34. The method as recited in claim 23 further comprising freezing the blood around the distal section to form ice which contacts the wall.

35. A method for ablating the renal artery to disrupt renal nerve function comprising the step of extracting heat from the renal artery by a single liquid phase cryogen to cool the renal nerve such that nerve function is disrupted.

36. The method of claim 35 further comprising accessing the renal artery endovascularly.

37. The method of claim 36 further comprising the step of remodeling the lumen of the renal artery subsequent to the applying step to maintain patency of the renal artery.

38. The method as recited in claim 36 further comprising the step of crystallizing blood within the renal artery.

39. The method of claim 35 further comprising accessing the renal hilum laparoscopically.

40. The method of claim 35 further comprising accessing the renal artery endovascularly and laparoscopically.

41. The method as recited in claim 35 wherein the extracting step creates a radially extending freeze depth commencing at the luminal surface of the renal artery and radially extending therefrom, said freeze depth being equal to or greater than 2 mm.

* * * * *